United States Patent
Liu et al.

(10) Patent No.: US 12,208,204 B2
(45) Date of Patent: Jan. 28, 2025

(54) METHOD OF DETECTING ERRORS IN THE CONNECTIONS IN A HUMIDIFICATION SYSTEM

(71) Applicant: Fisher & Paykel Healthcare Limited, Auckland (NZ)

(72) Inventors: Po-Yen Liu, Auckland (NZ); Ivan Chih-Fan Teng, Auckland (NZ); Peter Alan Seekup, Auckland (NZ); Daniel John Smith, Auckland (NZ); Ho Shing Lo, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/296,729

(22) Filed: Apr. 6, 2023

(65) Prior Publication Data

US 2023/0310779 A1     Oct. 5, 2023

Related U.S. Application Data

(63) Continuation of application No. 16/340,590, filed as application No. PCT/NZ2017/050132 on Oct. 11, 2017, now Pat. No. 11,684,736.

(Continued)

(51) Int. Cl.
*A61M 16/00* (2006.01)
*A61M 16/10* (2006.01)
*A61M 16/16* (2006.01)

(52) U.S. Cl.
CPC ...... *A61M 16/026* (2017.08); *A61M 16/0051* (2013.01); *A61M 16/022* (2017.08);

(Continued)

(58) Field of Classification Search
CPC .............. A61M 16/16; A61M 2205/18; A61M 2205/3368
See application file for complete search history.

(56) References Cited

U.S. PATENT DOCUMENTS

| 3,806,102 A | 4/1974 | Valenta et al. |
| 4,778,017 A | 10/1988 | Liang |

(Continued)

FOREIGN PATENT DOCUMENTS

| AU | 2012216775 | 3/2014 |
| AU | 2010206053 | 8/2014 |

(Continued)

OTHER PUBLICATIONS

Written Opinion in corresponding International Patent Application No. PCT/NZ2017/050132, dated Feb. 1, 2018, in 12 pages.

(Continued)

*Primary Examiner* — Joseph D. Boecker
*Assistant Examiner* — Thomas W Greig
(74) *Attorney, Agent, or Firm* — Knobbe, Martens, Olson & Bear, LLP

(57) ABSTRACT

Various control methods can indirectly determine incorrect connections between components in a respiratory therapy system. For example, errors in the connections can occur between a patient interface, a humidifier and/or a gases source. The methods can indirectly detect if a reverse flow condition exists or other error conditions. A reverse flow condition can occur when gases flows in a direction different from an intended direction of flow. The detection of the reverse flow condition can be indicative of likely errors in connections between the humidifier, patient interface and/or gases source.

20 Claims, 27 Drawing Sheets

Related U.S. Application Data

(60) Provisional application No. 62/406,720, filed on Oct. 11, 2016.

(52) U.S. Cl.
CPC .......... *A61M 16/109* (2014.02); *A61M 16/16* (2013.01); *A61M 2205/14* (2013.01); *A61M 2205/18* (2013.01); *A61M 2205/3368* (2013.01); *A61M 2205/502* (2013.01); *A61M 2205/581* (2013.01); *A61M 2205/583* (2013.01); *A61M 2205/70* (2013.01)

(56) References Cited

U.S. PATENT DOCUMENTS

| | | | |
|---|---|---|---|
| 5,307,243 A | 4/1994 | Sharp et al. | |
| 5,349,946 A | 9/1994 | McComb | |
| 5,359,179 A | 10/1994 | Desloge et al. | |
| 5,367,604 A * | 11/1994 | Murray | A61M 16/109 |
| | | | 392/394 |
| 5,379,650 A | 1/1995 | Kofoed et al. | |
| 5,782,233 A | 7/1998 | Niemi et al. | |
| 6,039,696 A | 3/2000 | Bell | |
| 6,554,260 B1 | 4/2003 | Lipscombe et al. | |
| 6,983,652 B2 * | 1/2006 | Blakley | G01F 1/696 |
| | | | 73/204.22 |
| 7,024,945 B2 | 4/2006 | Wallace | |
| 7,093,501 B2 | 8/2006 | Kuo et al. | |
| 7,525,663 B2 | 4/2009 | Kwok et al. | |
| 8,049,143 B2 | 11/2011 | Andel et al. | |
| 8,063,343 B2 | 11/2011 | Mcghin et al. | |
| 8,381,729 B2 | 2/2013 | Freitag et al. | |
| 8,733,349 B2 | 5/2014 | Bath et al. | |
| 9,937,314 B2 | 4/2018 | Buechi et al. | |
| 9,937,316 B2 | 4/2018 | Buechi et al. | |
| 9,943,108 B2 | 4/2018 | Lord | |
| 10,398,871 B2 | 9/2019 | Cortez, Jr. et al. | |
| 11,684,736 B2 | 6/2023 | Liu et al. | |
| 2002/0100320 A1 | 8/2002 | Smith et al. | |
| 2003/0116556 A1 | 6/2003 | Li | |
| 2006/0211981 A1 | 9/2006 | Sparks et al. | |
| 2007/0181127 A1 | 8/2007 | Jin et al. | |
| 2007/0265877 A1 | 11/2007 | Rice et al. | |
| 2007/0272239 A1 | 11/2007 | Aylsworth et al. | |
| 2008/0308100 A1 | 12/2008 | Pujol et al. | |
| 2009/0045829 A1 | 2/2009 | Awazu et al. | |
| 2009/0110379 A1 | 4/2009 | Mcghin et al. | |
| 2009/0194106 A1 | 8/2009 | Smith et al. | |
| 2010/0206308 A1 | 8/2010 | Klasek et al. | |
| 2011/0023874 A1 | 2/2011 | Bath et al. | |
| 2011/0049123 A1 | 3/2011 | Frock et al. | |
| 2011/0088693 A1 | 4/2011 | Somervell et al. | |
| 2011/0162647 A1 | 7/2011 | Huby et al. | |
| 2011/0253136 A1 | 10/2011 | Sweeney et al. | |
| 2012/0017904 A1 | 1/2012 | Ratto et al. | |
| 2012/0073573 A1 | 3/2012 | Thudor et al. | |
| 2012/0125333 A1 | 5/2012 | Bedford et al. | |
| 2012/0248636 A1 | 10/2012 | Fridberg et al. | |
| 2013/0081621 A1 | 4/2013 | Korneff et al. | |
| 2014/0202460 A1 | 7/2014 | Bath et al. | |
| 2014/0216459 A1 | 8/2014 | Vos et al. | |
| 2014/0238394 A1 | 8/2014 | Beuchi | |
| 2014/0261418 A1 | 9/2014 | Huang | |
| 2015/0048530 A1 * | 2/2015 | Cheung | A61M 16/024 |
| | | | 261/135 |
| 2015/0273175 A1 | 10/2015 | Acker et al. | |
| 2017/0266399 A1 | 9/2017 | Campana et al. | |
| 2018/0028773 A1 | 2/2018 | Klasek et al. | |
| 2020/0206442 A1 | 7/2020 | Knepper et al. | |
| 2022/0160977 A1 | 5/2022 | Teng et al. | |
| 2023/0302240 A1 | 9/2023 | Liu et al. | |

FOREIGN PATENT DOCUMENTS

| | | | |
|---|---|---|---|
| AU | 2017268523 A1 | 12/2017 | |
| CN | 205227470 U | 5/2016 | |
| EP | 1014527 A2 | 6/2000 | |
| EP | 2039387 A1 | 3/2009 | |
| EP | 2143459 | 1/2010 | |
| EP | 2229973 | 9/2010 | |
| EP | 2524714 | 11/2012 | |
| EP | 3139986 | 3/2017 | |
| GB | 2495771 | 7/2018 | |
| JP | H9-70437 A | 3/1997 | |
| JP | 2016118511 A | 6/2016 | |
| NZ | 587113 A | 12/2011 | |
| WO | WO 2000/027457 | 5/2000 | |
| WO | WO2003/048721 | 6/2003 | |
| WO | WO2006/092001 | 9/2006 | |
| WO | WO2008/055307 | 5/2008 | |
| WO | WO2008/091164 | 7/2008 | |
| WO | WO2009/085995 | 7/2009 | |
| WO | WO2010/031126 | 3/2010 | |
| WO | WO 2010/141983 A1 | 12/2010 | |
| WO | WO 2012/080941 A1 | 6/2012 | |
| WO | WO2012/135912 | 10/2012 | |
| WO | WO2012/164407 | 12/2012 | |
| WO | WO 2013/057146 A1 | 4/2013 | |
| WO | WO2013/147623 | 10/2013 | |
| WO | WO2013/165263 | 11/2013 | |
| WO | WO 2013/176557 A1 | 11/2013 | |
| WO | WO2014/052983 | 4/2014 | |
| WO | WO-2015038014 A1 * | 3/2015 | .......... A61M 16/022 |
| WO | WO2015/135040 | 9/2015 | |
| WO | WO 2017/027906 A1 | 2/2017 | |
| WO | WO2017/126980 | 7/2017 | |
| WO | WO 2017/126980 A2 | 7/2017 | |
| WO | WO 2018/070883 A1 | 4/2018 | |
| WO | WO 2020/204731 A1 | 10/2020 | |
| WO | WO 2022/023984 | 2/2022 | |

OTHER PUBLICATIONS

International Search Report in corresponding International Patent Application No. PCT/NZ2017/050132, dated Feb. 1, 2018, in 8 pages.

International Preliminary Report on Patentability in corresponding International Patent Application No. PCT/NZ2017/050132, dated Apr. 16, 2019, in 13 pages.

* cited by examiner

METHOD OF DETECTING ERRORS IN THE CONNECTIONS IN A HUMIDIFICATION SYSTEM

This application claims priority from provisional application U.S. 62/406,720 filed 11 Oct. 2016, the entire contents of which are hereby incorporated by reference.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD

The present application relates to a respiratory humidification system. In particular, the present application relates to detecting errors in the connections between components in the humidification system.

BACKGROUND

A number of methods can be used to supply humidified gases to a patient requiring breathing assistance. Such humidification systems generally include a source of pressurized air (or other mixture of gases) such as a ventilator, a humidifier including a source of water and a heating means to vaporize the water so as to humidify the gases from the gases source, and an inspiratory conduit to convey the humidified gases to a patient interface, such as a mask, a nasal cannula, and the like. Humidification systems can be single-limb or dual-limb. In a single-limb system, exhaled gases from the patient can be released into the ambient air via vent holes on the patient interface. In a dual-limb system, exhaled gases can be conveyed from the patient back to the gases source via an expiratory conduit.

SUMMARY

It is essential for proper functioning of a humidification system that the gases flow in a correct or normal direction from the gases source through the humidifier to the patient and that the components of the humidification system are connected correctly. The correct or normal direction can be a forward flow direction. The correct connections and normal flow direction can ensure that the gases are delivered to the patient at a desired humidity and a desired patient end temperature. Connection errors in the humidification system can occur between various components, for example, between two or more of the patient interface, humidifier and/or gases source. Connection errors in the humidification system can be due to a set up error. Caregivers can incorrectly couple conduits that have the corresponding end connectors of the same type, such as the 22 mm male and female medical taper connectors or other standard connectors. The caregiver can connect the humidifier and gases source backward. Proprietary connections may help ameliorate this issue, such as, for example, at the humidifier outlet, however this causes manufacturing complexities and increases costs, and/or may be confusing for the caregiver or user. Moreover, some connections may be standardized connectors required by regulations and/or by commercial necessity, which may not be feasibly changed to a proprietary connector. Other components of the humidification system can be incorrectly connected to each other.

The connection errors can result in reverse flow conditions. A reverse flow condition can be a condition when the gases flow in the wrong or reverse direction as compared to a desired direction, such as a forward flow direction. Incorrect connections of the components can result in the gases being delivered to the patient above or below a desired humidity and/or temperature, leading to unsatisfactory treatments, discomfort, and/or adverse reactions in the patient. For example, dry air can be delivered from the gases source directly to the patient, whereas humidified gases can be delivered to the gases source. In such an incorrect connection, exhaled air from the patient is delivered to the humidifier. In a reverse flow condition, damage can also occur to the gases source (for example, the ventilator or other gases source) due to provision of humidity to the gases source. The humidity provided to the gases source can cause condensate formation that can damage the gases source.

A reverse flow condition can be indicative of incorrect connections or an incorrect set up by a clinician or nurse. Current humidification systems cannot directly detect a reverse flow condition. This can be due to the use of an omni-directional flow sensor, which cannot directly detect the direction of the flow, and/or the humidification system having no indirect reverse flow detection methods in place. For example, other types of sensors present on current humidification systems, such as humidity sensors and/or infrared temperature sensors are not configured to detect a reverse flow condition or incorrect connections.

Some humidification systems can detect if the patient is exhaling through the inspiratory conduit by detecting a higher temperature at a humidifier inlet than at a gases source, and/or by comparing flow rates and/or power dissipation curves at the humidifier inlet and outlet. These detection features can help in identifying whether the system is single-limb or dual-limb. However, these detecting features are different from detecting incorrect connections described in the present disclosure. Such systems are described in U.S. Provisional Application No. 62/280,076 entitled "HUMIDIFICATION OF RESPIRATORY GASES," filed Jan. 18, 2016, and U.S. Provisional Application No. 62/362,709 entitled "HUMIDIFICATION OF RESPIRATORY GASES," filed Jul. 15, 2016, each of which is incorporated herein by reference in its entirety.

Some humidification systems can detect heating or flow rate anomalies in the system that can be caused by reverse flow conditions or other types of system malfunctions. The anomalies can include when the humidifier inlet temperature exceeds the humidifier outlet temperature by a predetermined threshold. Such systems are described in U.S. patent application Ser. No. 15/021,616 entitled "HUMIDIFICATION SYSTEM," filed Mar. 11, 2016, which is incorporated herein by reference in its entirety.

Some humidification systems can minimize errors in the connections of the components by having proprietary end connectors for dedicated tubes and conduits. For example, the inspiratory conduit can have a proprietary end connector that can only be connected to the humidifier outlet. However, these humidification systems cannot detect reverse flow conditions.

Humidification systems of the present disclosure can detect or automatically detect incorrect connections and alert a user. The systems can detect errors in the connections between components, including between patient interface, humidifier, and/or gases source, in the system. Humidification systems of the present disclosure can detect the existence of a reverse flow condition/situation where a patient is receiving sub-optimal humidity and/or temperature. The methods disclosed herein can detect if the gases are flowing in the wrong direction. The wrong direction can be a reverse flow direction. A reverse flow condition detected by the methods described herein likely indicates errors in the connections between the humidifier, patient interface, and/or gases source. The present disclosure also relates to detection of incorrect connection of the expiratory conduit in dual-limb systems, such as systems used for providing invasive mechanical ventilation therapies, noninvasive mechanical ventilation therapies, neonatal invasive or noninvasive therapies and/or other therapies. The incorrect connection can include improper connection and/or disconnection of the expiratory conduit, resulting in improper connection and/or disconnection of the expiratory conduit heat source. The expiratory conduit incorrect connection detection can include warning a user.

A method of detecting incorrect connections in a respiratory humidification system including a gases source, a humidifier including an inlet and an outlet, and an inspiratory conduit can comprise performing one or more reverse flow detection tests by comparing an inlet temperature measured by a sensor at the inlet of the humidifier with one or more of an outlet set point or an outlet temperature measurement measured by a sensor positioned at the outlet of the humidifier. The method can comprise outputting an indication of reverse flow conditions indicative of the incorrect connections when the inlet temperature is higher than one or more of the outlet set point or the outlet temperature measurement. The method can include alerting a user of the indication of reverse flow conditions. Alerting can comprise providing one or more audible alarms, text message, images, or a combination thereof. Alerting can also comprise providing instructions for resolving the reverse flow conditions. The humidification system can also comprise an expiratory conduit.

A respiratory humidification system with incorrect connection detection can comprise a gases source configured to provide a source of gases, a humidifier including an inlet and an outlet, the humidifier configured to humidify air and including a humidifier heat source to heat a liquid to humidify the gases provided by the gases source, and an inspiratory conduit configured to provide the humidified gases to a user. The gases source, humidifier and inspiratory conduit can form at least a part of a breathing circuit. The system can comprise sensors at the humidifier inlet and outlet configured to measure an inlet temperature and an outlet temperature, respectively, and a hardware and/or software controller. The hardware and/or software controller can be in electrical communication with the sensors and configured to output an indication of reverse flow conditions indicative of the incorrect connections when the inlet temperature is higher than one or more of an outlet set point or outlet temperature. The hardware and/or software controller can be configured to alert the user of the indication of reverse flow conditions. Alerting can comprise providing one or more audible alarms, text message, images, or a combination thereof. Alerting can also comprise providing instructions for resolving the reverse flow conditions. The humidification system can also comprise an expiratory conduit.

A method of detecting incorrect connections in a respiratory humidification system including a gases source, a humidifier including an inlet and an outlet, and an inspiratory conduit can comprise performing one or more reverse flow detection tests by comparing an inlet parameter measured by a first sensor at the inlet of the humidifier with an outlet parameter measured by a second sensor at the outlet of the humidifier. The method can comprise outputting an indication of reverse flow conditions when the inlet parameter is higher than the outlet parameter. The parameter can comprise a flow rate or a power dissipation value. The method can include alerting a user of the indication of reverse flow conditions. Alerting can comprise providing one or more audible alarms, text message, images, or a combination thereof. Alerting can also comprise providing instructions for resolving the reverse flow conditions.

A humidification system with detection mechanisms for incorrect connections can include a gases source configured to provide a source of gases, a humidifier including an inlet and an outlet, the humidifier configured to humidify air and including a humidifier heat source, such as, for example, a heater plate, to heat a liquid to humidify the gases provided by the gases source, and an inspiratory conduit configured to provide the humidified gases to a user. The gases source, humidifier and inspiratory conduit can form at least a part of a breathing circuit. The system can include sensors at the humidifier inlet and outlet and configured to measure an inlet parameter and an outlet parameter, respectively, and a hardware and/or software controller in electrical communication with the sensors. The hardware and/or software controller can be configured to output an indication of reverse flow conditions when the inlet parameter is higher than the outlet parameter. The parameter can comprise a flow rate or a power dissipation value. The hardware and/or software controller can be configured to alert the user of the indication of reverse flow conditions. Alerting can comprise providing one or more audible alarms, text message, images, or a combination thereof. Alerting can also comprise providing instructions for resolving the reverse flow conditions. The humidification system can also comprise an expiratory conduit.

A method of detecting incorrect connections in a respiratory humidification system can include performing one or more reverse flow detection tests by a hardware and/or software controller of the humidification system. The one or more reverse flow detection tests can include the steps of comparing a patient end temperature measured by a first sensor at a patient end of an inspiratory conduit of the humidification system with a patient end set point; when the patient end temperature is higher than the patient end set point, comparing an inlet temperature measured by a second sensor at an inlet of a humidifier of the humidification system with an outlet set point or an outlet temperature measured by a third sensor at an outlet of the humidifier; and outputting an indication of reverse flow conditions indicative of the incorrect connections when the inlet temperature is higher than the outlet set point or the outlet temperature. The method can include comparing the inlet temperature with an ambient temperature when the inlet temperature is higher than the outlet set point or the outlet temperature, and outputting the indication of reverse flow conditions when the inlet temperature is higher than the ambient temperature. The method can include alerting a user of the indication of reverse flow conditions. Alerting can comprise providing one or more audible alarms, text message, images, or a combination thereof. Alerting can also comprise providing instructions for resolving the reverse flow conditions. The humidification system can also comprise an expiratory conduit.

A humidification system with detection mechanisms for incorrect connections can include a gases source configured to provide a source of gases, a humidifier including an inlet and an outlet, the humidifier configured to humidify air and including a humidifier heat source to heat a liquid to humidify the gases provided by the gases source and an inspiratory conduit configured to provide the humidified gases to a user. The gases source, humidifier and inspiratory conduit can form at least a part of a breathing circuit. The system can include a first sensor at a patient end of the inspiratory conduit and configured to measure a patient end temperature, a second sensor at the humidifier inlet and configured to measure an inlet temperature, and a third sensor at the humidifier outlet and configured to measure an outlet temperature. The system can include a hardware and/or software controller in electrical communication with the first, second and third sensors. The hardware and/or software controller can be configured to detect an indication of reverse flow conditions indicative of the incorrect connections in the humidification system by: comparing the inlet temperature with an outlet set point or the outlet temperature when the patient end temperature is higher than the patient end set point, and outputting an indication of reverse flow conditions when the inlet temperature is higher than the outlet set point or the outlet temperature. The hardware and/or software controller can be configured to compare the inlet temperature with an ambient temperature when the inlet temperature is higher than the outlet set point or the outlet temperature, and to output the indication of reverse flow conditions when the inlet temperature is higher than the ambient temperature. The hardware and/or software controller can be configured to alert the user of the indication of reverse flow conditions. Alerting can comprise providing one or more audible alarms, text message, images, or a combination thereof. Alerting can also comprise providing instructions for resolving the reverse flow conditions. The humidification system can also comprise an expiratory conduit.

A method of detecting incorrect connections in a respiratory humidification system can include performing one or more reverse flow detection tests by a hardware and/or software controller of the humidification system. The one or more reverse flow detection tests can include the steps of comparing a patient end temperature measured by a first sensor at a patient end of an inspiratory conduit of the humidification system with a patient end set point; when the patient end temperature is lower than the patient end set point, comparing an outlet temperature measured by a second sensor at an outlet of a humidifier of the humidification system with the patient end temperature; and outputting an indication of reverse flow conditions when the outlet temperature is higher than the patient end temperature. The method can include alerting a user of the indication of reverse flow conditions. Alerting can comprise providing one or more audible alarms, text message, images, or a combination thereof. Alerting can also comprise providing instructions for resolving the reverse flow conditions. The humidification system can also comprise an expiratory conduit.

A humidification system with detection mechanisms for incorrect connections can include a gases source configured to provide a source of gases, a humidifier including an inlet and an outlet, the humidifier configured to humidify air and including a humidifier heat source to heat a liquid to humidify the gases provided by the gases source and an inspiratory conduit configured to provide the humidified gases to a user. The gases source, humidifier and inspiratory conduit can form at least a part of a breathing circuit. The system can include a first sensor at a patient end of the inspiratory conduit and configured to measure a patient end temperature and a second sensor at the humidifier outlet and configured to measure an outlet temperature. The system can include a hardware and/or software controller in electrical communication with the first and second sensors. The hardware and/or software controller can be configured to detect an indication of reverse flow conditions indicative of the incorrect connections in the humidification system by: comparing the outlet temperature with the patient end temperature when the patient end temperature is lower than the patient end set point, and outputting an indication of reverse flow conditions when the outlet temperature is higher than the patient end temperature. The hardware and/or software controller can be configured to alert the user of the indication of reverse flow conditions. Alerting can comprise providing one or more audible alarms, text message, images, or a combination thereof. Alerting can also comprise providing instructions for resolving the reverse flow conditions. The humidification system can also comprise an expiratory conduit.

A method of detecting incorrect connections in a respiratory humidification system can comprise providing a first electrical power to a humidifier heat source in a humidifier of the humidification system, comparing an inlet temperature measured by a first sensor at an inlet of a humidifier of the humidification system with an outlet temperature measured by a second sensor at an outlet of the humidifier, or a change in the inlet temperature with a change in the outlet temperature, and outputting an indication of reverse flow conditions indicative of the incorrect connections when the inlet temperature is higher than the outlet temperature or when the change in the inlet temperature is greater than the change in the outlet temperature. The method can comprise interrupting a therapy that is run on the humidification system. The therapy can be a respiratory/ventilation therapy and/or the humidification therapy. The first electrical power can be a maximum electrical power. The method can include alerting a user of the indication of reverse flow conditions. Alerting can comprise providing one or more audible alarms, text message, images, or a combination thereof. Alerting can also comprise providing instructions for resolving the reverse flow conditions. The humidification system can also comprise an expiratory conduit.

A humidification system with detection mechanisms for incorrect connections can include a gases source configured to provide a source of gases, a humidifier including an inlet and an outlet, the humidifier configured to humidify air and including a humidifier heat source to heat a liquid to humidify the gases provided by the gases source, and an inspiratory conduit configured to provide the humidified gases to a user. The gases source, humidifier and inspiratory conduit can form at least a part of a breathing circuit. The system can include a first sensor at the humidifier inlet and configured to measure an inlet temperature, a second sensor at the humidifier outlet and configured to measure an outlet temperature, and a hardware and/or software controller in electrical communication with the first and second sensors. The hardware and/or software controller can be configured to detect an indication of reverse flow conditions in the humidification system by provide a first electrical power to the humidifier heat source, and outputting an indication of reverse flow conditions when the inlet temperature is higher than the outlet temperature or when the change in the inlet temperature is greater than the change in the outlet temperature. The hardware and/or software controller can be configured to interrupt a therapy that is run on the humidification system when detect the indication of reverse flow conditions in the humidification system. The therapy can be a respiratory or ventilation therapy and/or a humidification therapy. The first electrical power can be a maximum electrical power. The hardware and/or software controller can be configured to alert the user of the indication of reverse flow conditions. Alerting can comprise providing one or more audible alarms, text message, images, or a combination thereof. Alerting can also comprise providing instructions for resolving the reverse flow conditions. The humidification system can also comprise an expiratory conduit.

A method of detecting incorrect connections in a respiratory humidification system can comprise providing a first electrical power to an inspiratory conduit heat source in an inspiratory conduit of the humidification system, comparing a patient end temperature measured by a first sensor at a patient end of the inspiratory conduit with an outlet temperature measured by a second sensor at an outlet of a humidifier of the humidification system, or a change in the patient end temperature with a change in the outlet temperature, and outputting an indication of reverse flow conditions when the patient end temperature is lower than the outlet temperature or when the change in the patient end temperature is less than the change in the outlet temperature. The method can comprise interrupting a therapy that is run on the humidification system. The therapy can be a respiratory or ventilation therapy and/or a humidification therapy. The first electrical power can be a maximum electrical power. The method can include alerting a user of the indication of reverse flow conditions. Alerting can comprise providing one or more audible alarms, text message, images, or a combination thereof. Alerting can also comprise providing instructions for resolving the reverse flow conditions. The humidification system can also comprise an expiratory conduit.

A humidification system with detection mechanisms for incorrect connections can include a gases source configured to provide a source of gases, a humidifier including an inlet and an outlet, the humidifier configured to humidify air and including a humidifier heat source to heat a liquid to humidify the gases provided by the gases source, and an inspiratory conduit configured to provide the humidified gases to a user. The gases source, humidifier and inspiratory conduit can form at least a part of a breathing circuit. The system can include a first sensor at a patient end of the inspiratory conduit and configured to measure a patient end temperature, a second sensor at the humidifier outlet and configured to measure an outlet temperature, and a hardware and/or software controller in electrical communication with the first and second sensors. The hardware and/or software controller can be configured to detect an indication of reverse flow conditions in the humidification system by provide a first electrical power to the inspiratory conduit heat source, and output an indication of reverse flow conditions when the patient end temperature is lower than the outlet temperature or when the change in the patient end temperature is less than the change in the outlet temperature. The hardware and/or software controller can be configured to interrupt a therapy that is run on the humidification system when detect the indication of reverse flow conditions in the humidification system. The therapy can be a respiratory or ventilation therapy and/or a humidification therapy. The first electrical power can be a maximum electrical power. The hardware and/or software controller can be configured to alert the user of the indication of reverse flow conditions. Alerting can comprise providing one or more audible alarms, text message, images, or a combination thereof. Alerting can also comprise providing instructions for resolving the reverse flow conditions. The humidification system can also comprise an expiratory conduit.

A method of detecting reverse flow in a respiratory humidification system can comprise using one or more hardware processors of the humidification system to control circuitry configured to power a heating element, providing electrical power to the heating element of the humidification system, the humidification system further comprising a gases source, a humidifier including an inlet and an outlet, and an inspiratory conduit including an inspiratory conduit heat source, the humidifier further including a humidifier heat source; comparing a first temperature gradient measured by a first sensor downstream of the heating element with a second temperature gradient measured by a second sensor upstream of the heating element, the first and second sensors in electrical communication with the one or more hardware processors; and outputting to a display of the humidification system an indication of reverse flow conditions when the second temperature gradient is higher than the first temperature gradient. The display can comprise a screen, such as an LED screen or any other types of screens, audio alarm, and/or any other ways to alert a user as described herein. The method further comprise providing another electrical power to the humidifier heat source of the humidifier of the humidification system; receiving sensor data from a humidifier heat source temperature sensor at or near the humidifier heat source, the humidifier heat source temperature sensor in electrical communication with the one or more hardware processors; comparing a temperature gradient at the humidifier heat source with a threshold temperature gradient; and outputting to the display of the humidification system an indication of humidifier water-out condition when the temperature gradient at the humidifier heat source is higher than the threshold temperature gradient. The threshold temperature gradient can change based at least in part on flow rate, type of humidifier, any other system parameters, and/or any other ambient conditions. The method can be performed from a start-up condition.

A respiratory humidification system with reverse flow detection from a start-up condition can comprise a gases source configured to provide a source of gases, a humidifier including an inlet and an outlet, the humidifier configured to humidify air and further including a humidifier heat source to heat a liquid to humidify the gases provided by the gases source, an inspiratory conduit configured to provide the humidified gases to a user and including an inspiratory conduit heat source, the gases source, humidifier and inspiratory conduit forming at least a part of a breathing circuit, a first sensor downstream of the humidifier heat source and/or the inspiratory conduit heat source and configured to measure a first temperature; a second sensor upstream of the humidifier heat source and/or the inspiratory conduit heat source and configured to measure a second temperature; and a hardware and/or software controller, the hardware and/or software controller in electrical communication with the first and second sensors, the hardware and/or software controller configured to detect an indication of reverse flow conditions in the humidification system by: providing an electrical power to the humidifier heat source and/or the inspiratory conduit heat source; comparing a first temperature gradient at the first sensor with a second temperature gradient at the second sensor; and outputting an indication of reverse flow conditions when the second temperature gradient is higher than the first temperature gradient. The first sensor can be located at the humidifier outlet or the humidifier inlet. The second sensor can be located at a patient end of the inspiratory conduit or the humidifier outlet. The hardware and/or software controller can be further configured to detect a humidifier water-out condition by providing another electrical power to the humidifier heat source; receiving sensor data from a humidifier heat source temperature sensor at or near the humidifier heat source, the humidifier heat source temperature sensor in electrical communication with the one or more hardware processors; comparing a temperature gradient at the humidifier heat source with a threshold temperature gradient; and outputting an indication of humidifier water-out condition when the temperature gradient at the humidifier heat source is higher than the threshold temperature gradient. The threshold temperature gradient can change based at least in part on flow rate, type of humidifier, any other system parameters, and/or any other ambient conditions. The hardware and/or software controller can be configured to detect an indication of reverse flow conditions from a start-up condition.

A method can detect disconnection of an expiratory conduit heat source in a dual-limb respiratory humidification system. The system can comprise an expiratory conduit having the expiratory conduit heat source, an inspiratory conduit having a segmented inspiratory conduit heat source, a first heat source driver configured to energize the expiratory conduit heat source and at least a segment of the inspiratory conduit heat source, and a second heat source driver configured to energize the expiratory conduit heat source and at least another segment of the inspiratory conduit heat source. The method can comprise using one of the first and second heat source drivers, providing a voltage across the expiratory and inspiratory conduit heat sources; monitoring a current detected by the one of the first and second heat source drivers; and outputting an indication of inspiratory conduit heat source disconnection when the current deviates from an expected value by a predetermined tolerance, or shows a sudden change above or below a threshold. The method can further comprise exiting an ongoing therapy mode; reconnecting the first and second heat source drivers so that one of the first and second drivers is configured to energize the expiratory conduit heat source and another one of the first and second drivers is configured to energize the inspiratory conduit heat source; using the one of the first and second heat source drivers, providing a second voltage across the expiratory conduit heat source; monitoring a current detected by the one of the first and second heat source drivers; and outputting an indication of expiratory conduit heat source disconnection when the current is at or near zero. The second voltage can comprise a low duty cycle or a minimum power. Activation of the method can be configured to be adjustable. A method can also detect disconnection of the expiratory conduit heat source by detecting a presence of a circuit ID resistor when a hardware and/or software controller applies a power across the expiratory conduit heat source. The system can determine that the expiratory conduit heat source is disconnected when the circuit ID resistor cannot be detected.

A dual-limb respiratory humidification system with expiratory conduit heat source disconnection detection can comprise a breathing circuit having a gases source configured to provide a source of gases, a humidifier configured to heat a liquid to humidify the gases provided by the gases source, an inspiratory conduit configured to provide the humidified gases to a user from the humidifier and including a segmented inspiratory conduit heat source, and an expiratory conduit configured to provide exhaled gases from the user to the gases source and including an expiratory conduit heat source; a first heat source driver configured to energize the expiratory conduit heat source and at least a segment of the inspiratory conduit heat source; and a second heat source driver configured to energize the expiratory conduit heat source and at least another segment of the inspiratory conduit heat source, wherein at least one of the first and second heat source drivers is configured to detect an indication of expiratory conduit heat source disconnection by providing a voltage across the expiratory and inspiratory conduit heat sources; detecting a current; and outputting an indication of inspiratory conduit heat source disconnection when the current deviates from an expected value by a predetermined tolerance, or shows a sudden change above or below a threshold. The system can be configured to switch configurations of the first and second heat source drivers so that one of the first and second drivers is configured to energize the expiratory conduit heat source and another one of the first and second drivers is configured to energize the inspiratory conduit heat source, the one of the first and second drivers configured to provide a second voltage across the expiratory conduit heat source; detected a current; and outputting an indication of expiratory conduit heat source disconnection when the current is at or near zero. The second voltage can comprise a low duty cycle or a minimum power. The system can be configured to detect an indication of expiratory conduit heat source disconnection at adjustable intervals. The system can also detect disconnection of the expiratory conduit heat source by detecting a presence of a circuit ID resistor when a hardware and/or software controller applies a power across the expiratory conduit heat source. The system can determine that the expiratory conduit heat source is disconnected when the circuit ID resistor cannot be detected.

A method can detect disconnection of an expiratory conduit heat source in a dual-limb respiratory humidification system. The system can comprise an expiratory conduit having the expiratory conduit heat source, an inspiratory conduit having a segmented inspiratory conduit heat source, a first heat source driver configured to energize the expiratory conduit heat source, and a second heat source driver configured to energize the inspiratory conduit heat source. The method can comprise using the first heat source driver, providing a voltage across the expiratory conduit heat source; monitoring a current detected by the first heat source driver; and outputting an indication of expiratory conduit heat source disconnection when the current is at or near zero.

A dual-limb respiratory humidification system with expiratory conduit heat source disconnection detection can comprise a breathing circuit having a gases source configured to provide a source of gases, a humidifier configured to heat a liquid to humidify the gases provided by the gases source, an inspiratory conduit configured to provide the humidified gases to a user from the humidifier and including an inspiratory conduit heat source, and an expiratory conduit configured to provide exhaled gases from the user to the gases source and including an expiratory conduit heat source; a first heat source driver configured to energize the expiratory conduit heat source; and a second heat source driver configured to energize the inspiratory conduit heat source, wherein the first heat source driver is configured to detect an indication of expiratory conduit heat source disconnection by provide a voltage across the expiratory conduit heat source; detected a current; and outputting an indication of expiratory conduit heat source disconnection when the current is at or near zero.

A method can detect reverse flow in a respiratory humidification system using transient system parameters. The respiratory humidification system can comprise a gases source, a humidifier including an inlet and an outlet, an inspiratory conduit, and a plurality of sensors. The method can comprise receiving transient state inputs from one or more of the plurality of sensors and/or system parameters of the respiratory humidification system; determining a reverse flow prediction indicator based at least in part on the inputs and/or system parameters; outputting an indication of reverse flow conditions when the reverse flow prediction indicator exceeds zero. The plurality of sensors can comprise more than one of a humidifier inlet temperature and/or flow rate sensor, a humidifier outlet temperature and/or flow rate sensor, a patient end temperature sensor, and/or a humidifier heat source temperature sensor. The received inputs can be from a transient state or steady state. The system parameters can comprise more than one of a humidifier heat source power, a humidifier outlet set point temperature, a patient end set point temperature, and/or power of at least a segment of an inspiratory conduit heat source. The reverse flow prediction indicator can be determined based at least in part on more than one parameter. The reverse flow prediction indicator can be determined at least in part on a humidifier inlet temperature, an absolute value of a difference between a humidifier outlet temperature and a humidifier outlet set point, a ratio of a flow rate to a humidifier heat source power, a ratio of the humidifier inlet temperature to the humidifier outlet set point, and a ratio of the humidifier inlet temperature to a tube temperature. The reverse flow prediction indicator can be determined at least in part on a filtered or unfiltered flow rate, an absolute value of a difference between a humidifier outlet temperature and a humidifier outlet set point, a ratio of a humidifier inlet temperature to a tube temperature, and a ratio of a filtered or unfiltered power of a segment of an inspiratory conduit heat source to a humidifier heat source temperature.

A respiratory humidification system with reverse flow detection can comprise a gases source configured to provide a source of gases; a humidifier including an inlet and an outlet, the humidifier configured to humidify air and further including a humidifier heat source to heat a liquid to humidify the gases provided by the gases source; an inspiratory conduit configured to provide the humidified gases to a user, the gases source, humidifier and inspiratory conduit forming at least a part of a breathing circuit; a plurality of sensors; and a hardware and/or software controller, the hardware and/or software controller in electrical communication with the plurality of sensors, the hardware and/or software controller configured to detect an indication of reverse flow conditions in the humidification system by receiving transient state inputs from one or more of the plurality of sensors and/or system parameters of the respiratory humidification system; determining a reverse flow prediction indicator based at least in part on the inputs and/or system parameters; outputting an indication of reverse flow conditions when the reverse flow prediction indicator exceeds zero. The plurality of sensors can comprise more than one of a humidifier inlet temperature and/or flow rate sensor, a humidifier outlet temperature and/or flow rate sensor, a patient end temperature sensor, and/or a humidifier heat source temperature sensor. The received inputs can be from a transient state or steady state. The system parameters can comprise more than one of a humidifier heat source power, a humidifier outlet set point temperature, a patient end set point temperature, and/or power of at least a segment of an inspiratory conduit heat source. The reverse flow prediction indicator can be determined based at least in part on more than one parameter. The reverse flow prediction indicator can be determined at least in part on a humidifier inlet temperature, an absolute value of a difference between a humidifier outlet temperature and a humidifier outlet set point, a ratio of a flow rate to a humidifier heat source power, a ratio of the humidifier inlet temperature to the humidifier outlet set point, and a ratio of the humidifier inlet temperature to a tube temperature. The reverse flow prediction indicator can be determined at least in part on a filtered or unfiltered flow rate, an absolute value of a difference between a humidifier outlet temperature and a humidifier outlet set point, a ratio of a humidifier inlet temperature to a tube temperature, and a ratio of a filtered or unfiltered power of a segment of an inspiratory conduit heat source to a humidifier heat source temperature.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Example Reverse Flow Conditions in Humidification Systems

Figure 1:
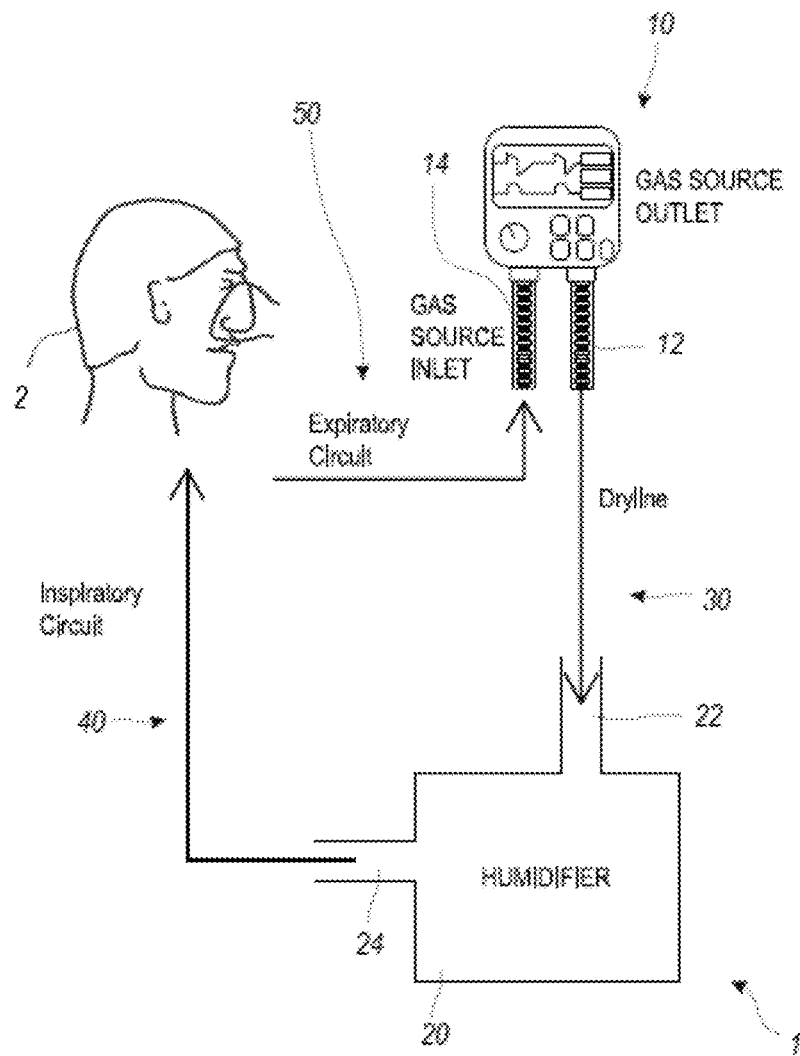
FIG. 1 illustrates a schematic representation of a dual-limb humidification system.

FIG. 1 illustrates a schematic representation of an example dual-limb humidification system 1. The humidification system 1 can comprise a gases source 10 in fluid communication with a humidifier 20 via a dryline conduit 30. The humidifier 20 can comprise various components, including, for example, a water chamber, and a heat source. The heat source can comprise a humidifier heat source. Examples of the humidifier heat source can include chemical heaters, radiant heaters, induction heaters, and the like. By way of example, the heat source can be a heater plate using a resistive heater. The humidifier 20 can also optionally comprise one or more processors, such as hardware and/or software processors. The gases source can be single direction gases sources, high flow sources, blower, ventilator unit, compressed air tanks, hospital wall gases sources, oxygen bottles, or pressurized gas bottles. The gases source can also be a flow source that may provide a flow of air. The gases source can also include a high flow gases source configured to deliver high flow of air or gases, for example, in excess of 30 L/min and/or up to 150 L/min. Gases supplied by the gases source can include either dry air, ambient air, oxygen, and/or a mixture of therapeutic or breathing gases. A controller can control the gases source 10 to generate a gases flow at a desired flow rate, temperature, and/or pressure. The gases from a gases source outlet 12 can comprise dry gases.

The dry gases can be provided to a humidifier inlet 22 via the dryline conduit 30. The humidifier inlet 22 can comprise a humidifier inlet temperature sensor and/or flow sensor. The humidifier 20 can contain a liquid, such as water. The humidifier 20 can have a heat source such as a heater plate for vaporizing the water to humidify and heat the dry gases from the dryline conduit 30. Water can be supplied to the humidifier 20 from a water source. The humidified gases can leave a humidifier outlet 24 and enter an inspiratory conduit 40. The humidifier outlet 24 can comprise a humidifier outlet temperature sensor and/or flow sensor.

The inspiratory conduit 40 can provide the humidified gases to a patient 2. The inspiratory conduit 40 can be coupled to a patient interface. Although the patient 2 is illustrated as wearing a mask in FIGS. 1, 2A-D, and 5A, a person of ordinary skill in the art would appreciate from the disclosure herein that the patient 2 can be wearing other types of patient interfaces disclosed herein, such as a nasal cannula. The patient interface can also comprise an interface tube, which is a short section of unheated tube, and the inspiratory conduit 40 can be coupled or connected to the interface tube. A patient interface end of the inspiratory conduit 40 can comprise a patient end temperature sensor and/or flow sensor. The inspiratory conduit 40 can have an inspiratory heat source to reduce or prevent condensate formation. Examples of the inspiratory conduit heat source can include a heater wire, heating tape, and/or water jacket heating. Condensate can be formed when a temperature of the humidified gases leaving the humidifier 20 drops due to heat loss when the gases travel through an unheated inspiratory conduit 40. The humidification system 1 can include an expiratory conduit 50. The expiratory conduit 50 can direct gases expired from the patient 2 back to a gases source inlet 14. The expiratory conduit 50 can include an expiratory conduit heat source, such as a heater wire, heating tape, and/or water jacket heating.

Sensors can be placed in various locations in the humidification system. For example, the sensors can include flow rate, pressure, temperature, and/or humidity sensors. The sensors can comprise a thermistor. The thermistor can act as a temperature sensor and can be switched to act as a flow sensor by applying a voltage to the thermistor to heat the thermistor. Output of the sensors can be received by the controller to assist the controller to operate the humidification system 1 in a manner that can provide optimal therapy. Other sensors that may be used include thermocouples, thermostats, semiconductor sensors, infrared sensors, and resistive temperature devices.

Figure 2A:
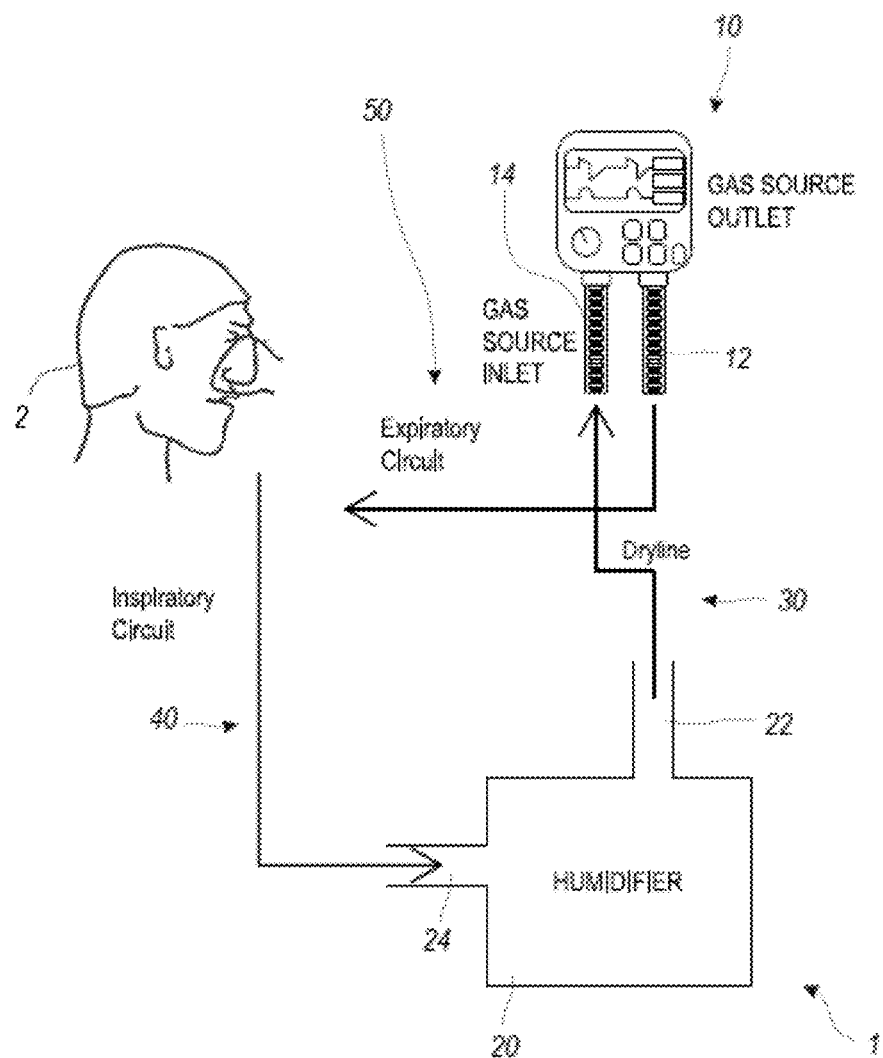
FIGS. 2A-D illustrate example reverse flow conditions and/or incorrect connections in the humidification system of FIG. 1.

Examples of reverse flow conditions and errors in the connections of the humidification system 1 components will now be described with respect to FIGS. 2A-D. These are examples only, and it should be appreciated that other conduit connection errors may be possible, such as connecting conduits backwards and/or in different locations in the circuit to where they should normally be connected. In Error 1 as shown in FIG. 2A, connections of the dryline conduit 30 and the expiratory conduit 50 with the gases source 10 are reversed. Specifically, the dryline conduit 30 is incorrectly coupled to the gases source inlet 14 and the expiratory conduit 50 is incorrectly coupled to the gases source outlet 12. As a result, the dry gases can flow directly to the patient 2 in the expiratory conduit 30 without being humidified or heated because the dry gases do not pass through the humidifier 20. The dry gases can be heated by an expiratory heat source in the expiratory conduit 50, wherein the heating is not properly regulated by the controller. Expired gases from the patient 2 can become humidified through the humidifier 30 before returning to the gases source 10.

Figure 2B:
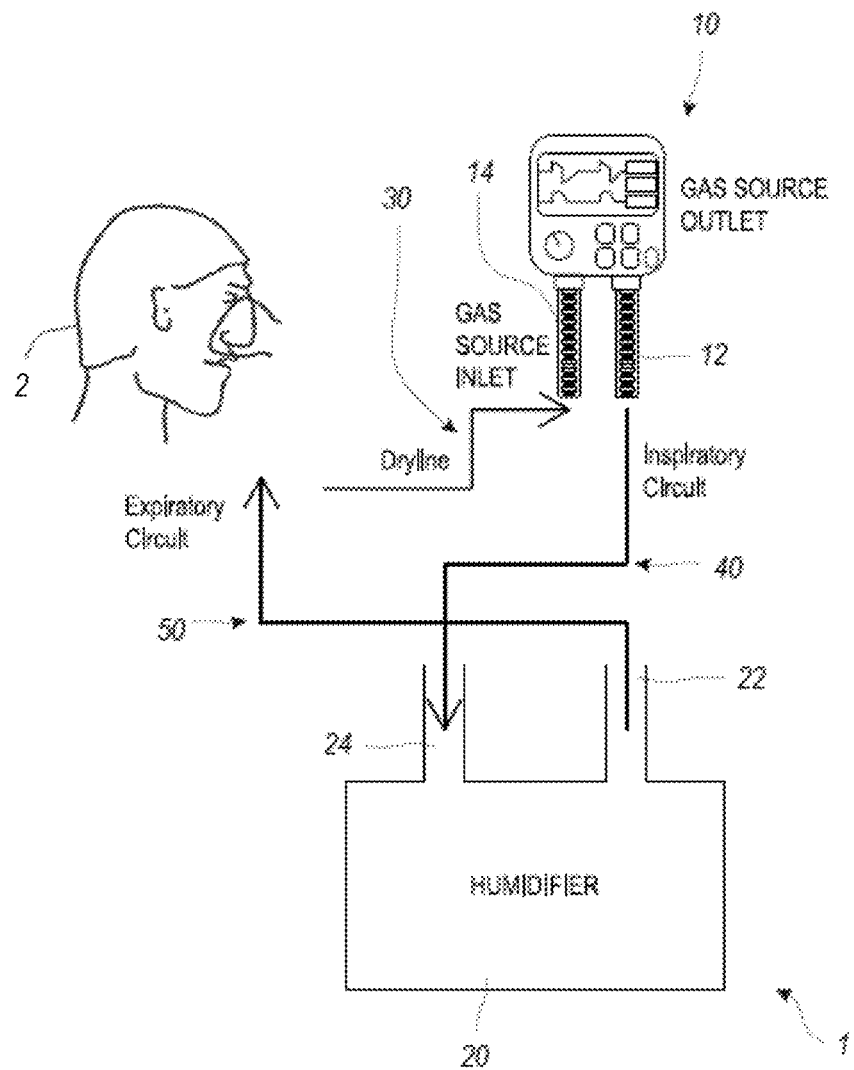

In Error 2 as shown in FIG. 2B, there is a reverse flow condition in the humidifier 20. Specifically, the inspiratory conduit 40 is incorrectly coupled to the gases source outlet 12 and the humidifier outlet 24. The expiratory conduit 50 is incorrectly coupled to the humidifier inlet port 22 and the patient 2. The dryline conduit 30 is incorrectly coupled to the patient 2 and the gases source inlet 14. The system receives outputs from the patient end sensor in the inspiratory conduit 40 and the sensors at the humidifier inlet and/or outlet 22, 24 that are not indicative of the actual patient end temperature, and/or inlet/outlet temperatures. The humidifier heat source and the inspiratory heat source may not function properly because of the incorrect outputs from the sensors. The gases leaving the humidifier inlet 22 for the patient 2 may not be heated because the expiratory conduit 50 may not have a heating wire, or may be heated by an expiratory conduit heat source in the expiratory conduit 50, wherein the heating is not properly regulated by the controller.

Figure 2C:
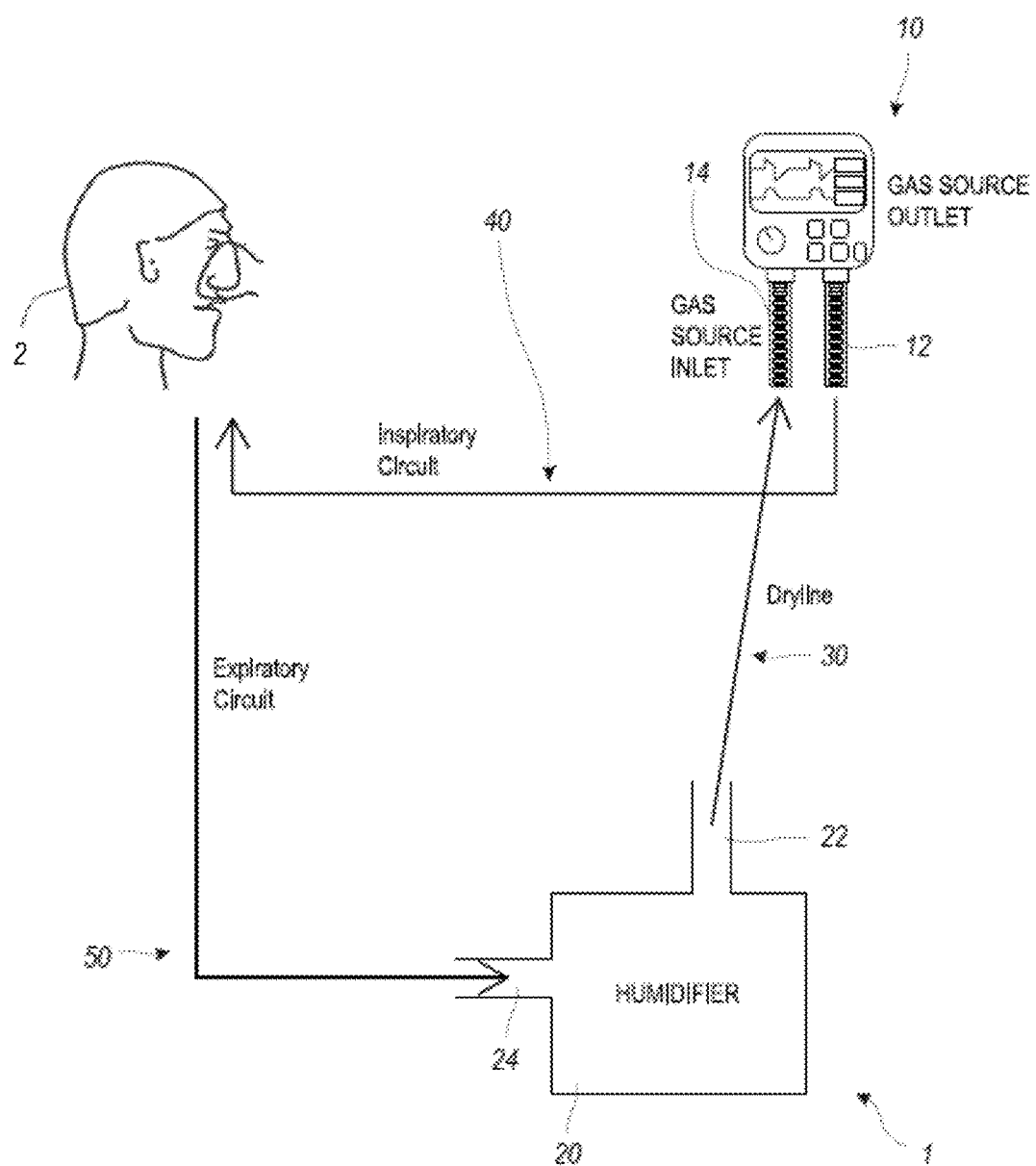

In Error 3 as shown in FIG. 2C, connections of the gases source inlet 14 and outlet 12 are reversed. Specifically, the dryline conduit 30 is incorrectly coupled to the gases source inlet 14 and the humidifier inlet 22. The expiratory conduit 50 is incorrectly coupled to the humidifier outlet 24 and the patient 2. The inspiratory conduit 40 is incorrectly coupled to the patient 2 and the gases source inlet 12. As a result, the dry gases can flow directly to the patient 2 in the expiratory conduit 30 without being humidified or heated because the dry gases do not pass through the humidifier 20. The expired gases from the patient 2 can become humidified in the humidifier 30 before returning to the gases source 10.

Figure 2D:
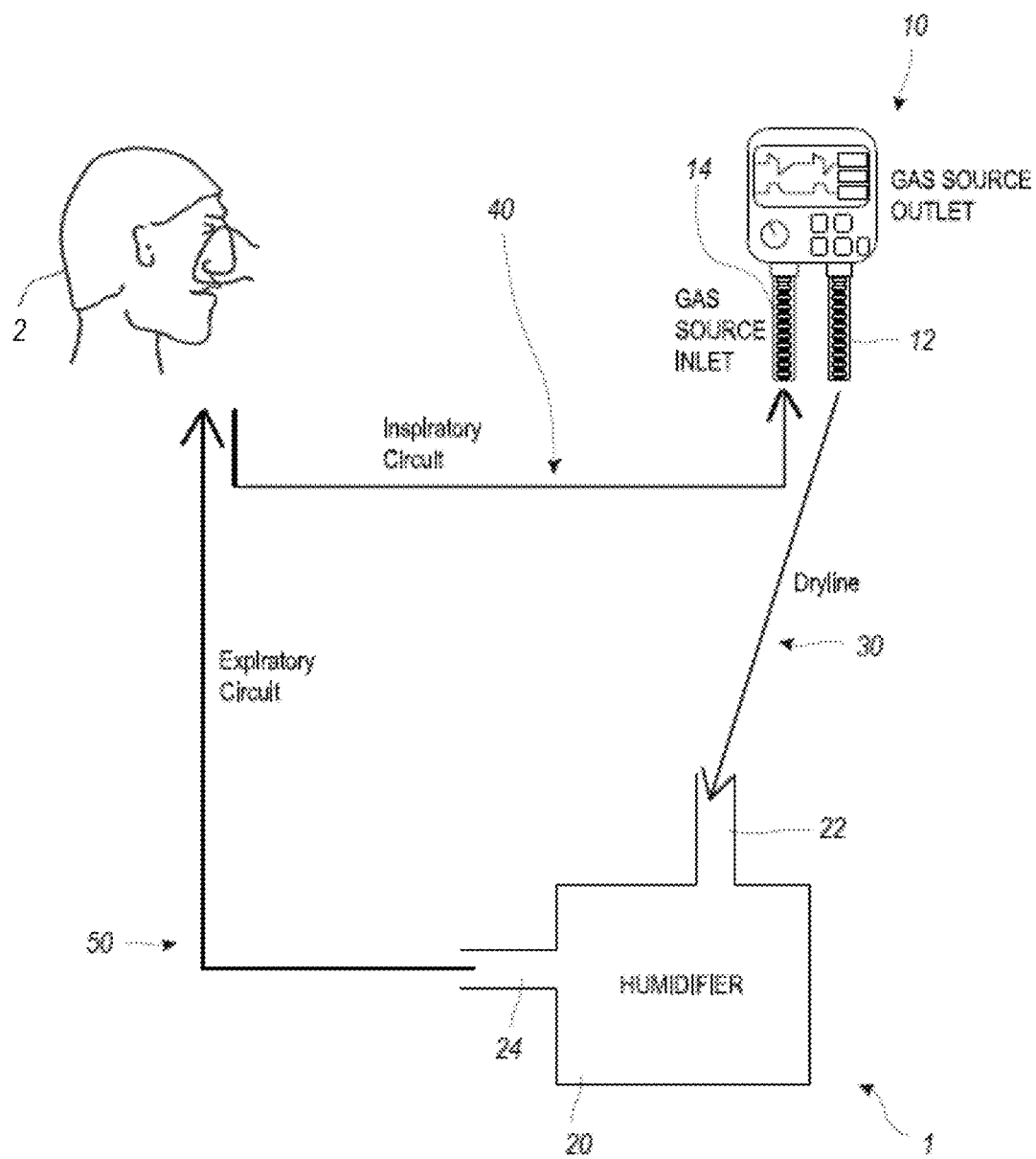

In Error 4 as shown in FIG. 2D, the gases flow in the normal direction, but there are errors in the connections. Specifically, the expiratory conduit 50 is incorrectly coupled to the humidifier outlet 24 and the patient 2. The inspiratory conduit 40 is incorrectly coupled to the gases source inlet 14 and the patient 2. As a result, the patient end sensor in the inspiratory conduit 40 cannot properly measure the temperature of the gases delivered to the patient 2, but measures the temperature of the exhaled gases from the patient 2. The gases leaving the humidifier 20 cannot be heated to ensure that the patient end temperature reaches the patient end set point. This can be due to the expiratory conduit 50 not having a heat source, or the expiratory conduit heat source not being properly energized by the controller receiving the patient end temperature input from the sensor in the inspiratory conduit 40. The gases reaching the patient 2 can exceed or fall below the patient end set point as the gases travel through the expiratory conduit 50.

Figure 3A:
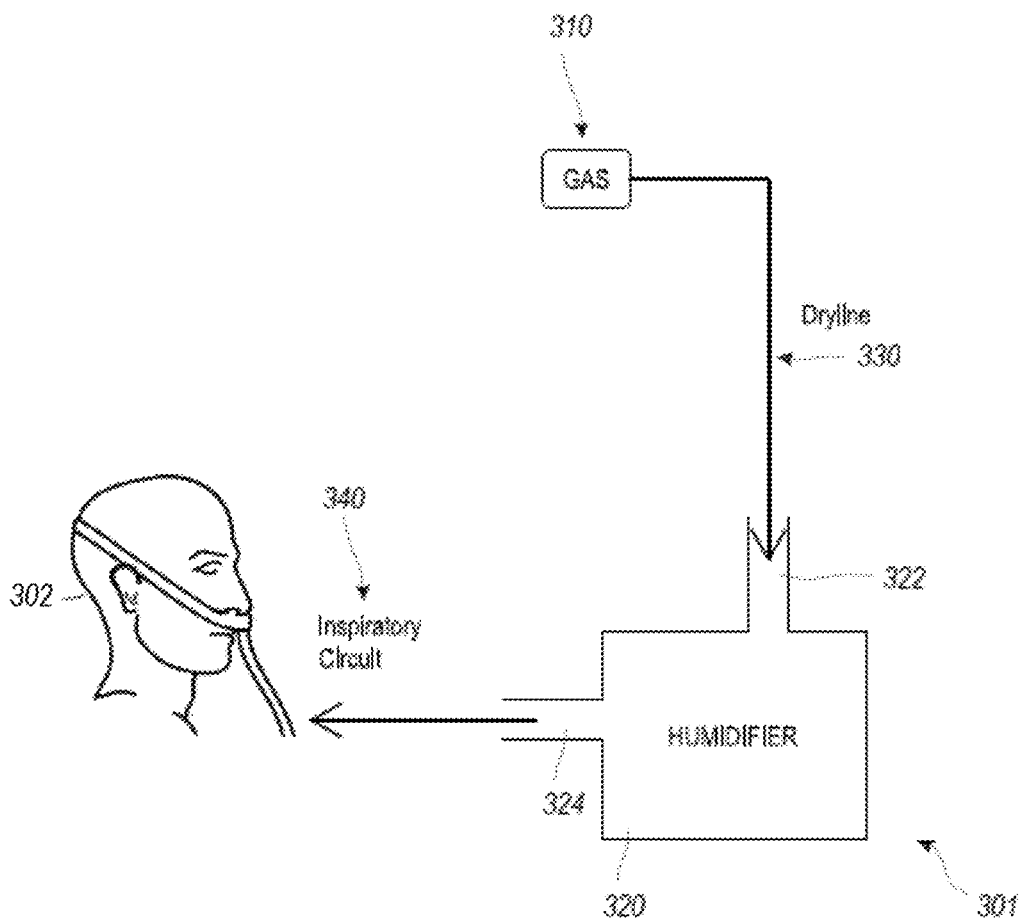
FIG. 3A illustrates a schematic representation of a single-limb humidification system.

Turning to FIG. 3A, a single-limb humidification system 301 can have the same features as the dual-limb humidification system 1 of FIG. 1A except as described below. The single-limb humidification system 301 can have a gases source 310 that has an outlet for gases outflow but no inlet for gases inflow. The single-limb humidification system 301 may not have an expiratory conduit. Exhaled gases from the patient 302 can exit through vent holes on the patient interface as described above and/or from the patient's mouth.

Figure 3B:
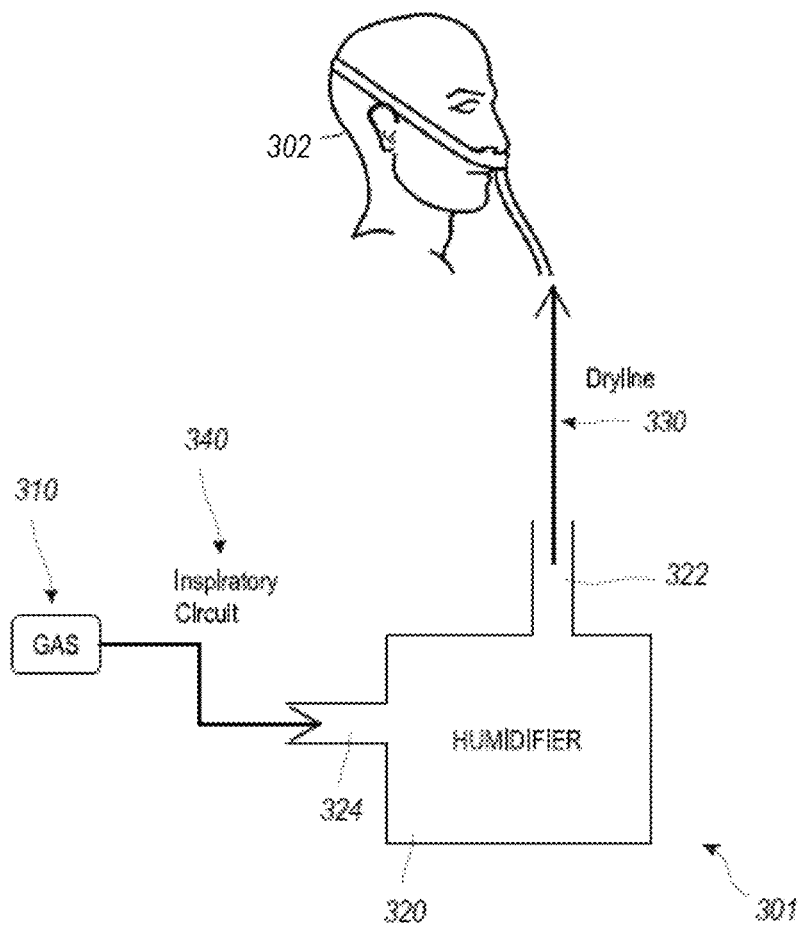
FIG. 3B illustrates an example reverse flow condition and/or incorrect connections in the humidification system of FIG. 3A.

In Error 5 as shown in FIG. 3B, the flow is reversed throughout the single-limb humidification system 301. Specifically, the inspiratory conduit 340 is incorrectly coupled to the gases source 310 and the humidifier outlet 324. The dryline conduit 330 is incorrectly coupled to the humidifier inlet 322 and the patient 302. As a result, the system receives outputs from the patient end sensor in the inspiratory conduit 340 and the sensors at the humidifier inlet and/or outlet 322, 324 that are not indicative of the actual patient end temperature, and/or inlet/outlet temperatures. The humidifier heat source and the inspiratory conduit heat source may not function properly because of the incorrect outputs from the sensors. The dry gases from the gases source 310 may be not be properly humidified by the humidifier 320 due to the incorrect sensor outputs. The gases leaving the humidifier 320 and entering the dryline conduit 330 cannot be heated because the dryline conduit 330 does not have an inspiratory conduit heat source. The gases reaching the patient 302 may fall below the patient end set point as the gases travel through the unheated dryline conduit 330. There can be condensate formation in the dryline conduit 330.

Overview of Humidification Systems with Reverse Flow Detection

The present disclosure relates to methods and systems of detecting reverse flow conditions and errors in the connections of the components in respiratory humidification systems.

Figure 4:
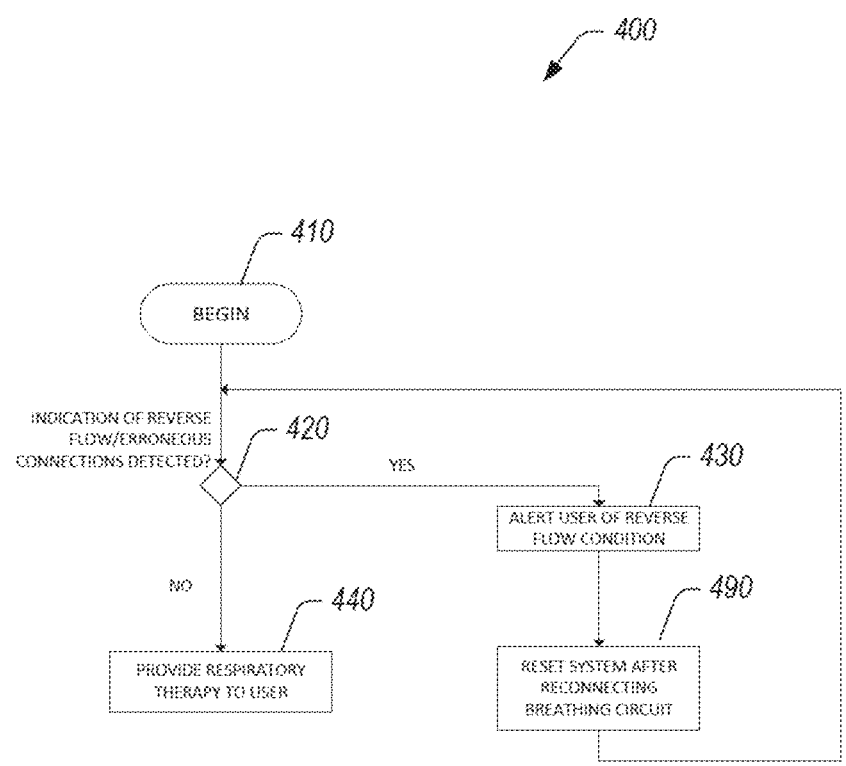
FIG. 4 illustrates a flow chart of an exemplary respiratory therapy treatment using a humidification system with control methods for detecting reverse flow.

As shown in FIG. 4, a humidification system, for example, the humidification systems 1, 301 of FIGS. 1 and 3A, begins 410 a respiratory treatment for the patient by activating the humidification system. The humidification system may need to set up by a caregiver, such as a nurse, or by the patient. Setting up the humidification system can involve connecting the components of the humidification system with the various conduits described herein. Upon activation, a controller of the humidification system can implement a reverse flow detection process at step 420 to determine if there is an indication of reverse flow conditions. One of ordinary skill in the art can appreciate that the reverse flow detection process can be run by the controller throughout the course of an operation of the humidification system and not necessarily only at the setup stage. The indication of reverse flow conditions can indicate likely errors in the connections of the components in the humidification system. The controller can implement any suitable reverse flow detection method, as such those described herein, or a combination thereof. The controller can also implement an appropriate reverse flow detection method or process based on a specific therapy mode, which will be described in detail below.

Even if the controller can determine an indication of reverse flow conditions at the step 420, it can be difficult to know if a reverse flow condition exists or if the sensors/probes have been removed. For those systems, the controller can run a probe-out test before implementing the reverse flow detection process at the step 420. The probe-out test can also instruct the controller to heat up the system and monitor if there is a rise in the tube temperature.

If an indication of reverse flow and/or incorrect setup/connections, and/or circuit disconnection conditions is determined, the humidification system can alert 430 the patient/caregiver (hereinafter referred to as "user"). For example, the controller can output an error message, an audible alarm sound/buzz, flashing of an error indicator light, or other like methods of alarming the user. The message from the controller can also indicate the components that likely have been incorrectly connected. A text-based and/or image-based message, and/or animation of troubleshooting can be displayed explaining the likely incorrect connections. An animation and/or a series of images illustrating how to correct the error can be displayed on the screen. The animation and/or series of images can be displayed on repeat until the system detects correct conditions and correct flow direction of gases, or until a user has inputted that the error has been corrected.

The controller can optionally be equipped with a counter, which can be hardware implemented and/or software implemented. The counter can add a count every time an indication of reverse flow conditions is determined. The counter can be a timer that can detect a length of time an indication of reverse flow conditions exists. The counter can be initialized every time an indication of reverse flow conditions is detected and can be disabled every time a normal flow condition is detected. The counter or timer may be used incrementally up to a threshold, such that the system may alert the user with an alarm as disclosed elsewhere herein once the threshold is reached or exceeded. Alternatively or in addition, a filter can be used, including but not limited to an (FIR/IIR) filter.

After being notified of the reverse flow condition, the user can reconnect a breathing circuit of the humidification system in a correct configuration. The user can reset 490 the humidification system after reconnecting the breathing circuit. The controller can also optionally automatically reset 490 upon reconnecting the breathing circuit. The controller can run the reverse flow detection process of the step 420 for the reconnected breathing circuit. If the controller can still detect an indication of reverse flow conditions, the controller can output another alert 430 to the user. If the controller can no longer detect an indication of reverse flow conditions, the controller can proceed to provide the respiratory therapy 440 or resume an interrupted therapy to the patient.

Implementing the reverse flow detection processes during set up of the system can allow detection of connection errors before the patient begins therapy. Correcting the connection errors during initial set-up can advantageously improve system performance by reducing condensate in the inspiratory conduit, providing optimal therapy to the patient, and/or improve patient safety by reducing the likelihood of providing dry and cold air directly to the patient, which can cause discomfort and/or more serious adverse reactions in the patient.

Various processes of detecting the reverse flow conditions and/or errors in the connections will now be described. The processes can be based on differential measurements of temperature, flow rate, and/or power dissipation at various locations of the humidification system. The processes described herein can include active and passive processes. The passive processes can work in the background to determine a reverse flow condition. The active processes can disrupt the respiratory and/or humidification therapy to determine if a reverse flow condition is present. The disruption can be brief and/or significant compared to a duration of the respiratory therapy. The active processes can override the normal operation or control of the system. For example, the active processes can override controls of the inspiratory and/or expiratory conduit heat source, and/or the humidifier heat source, and/or the sensor.

Figure 5A:
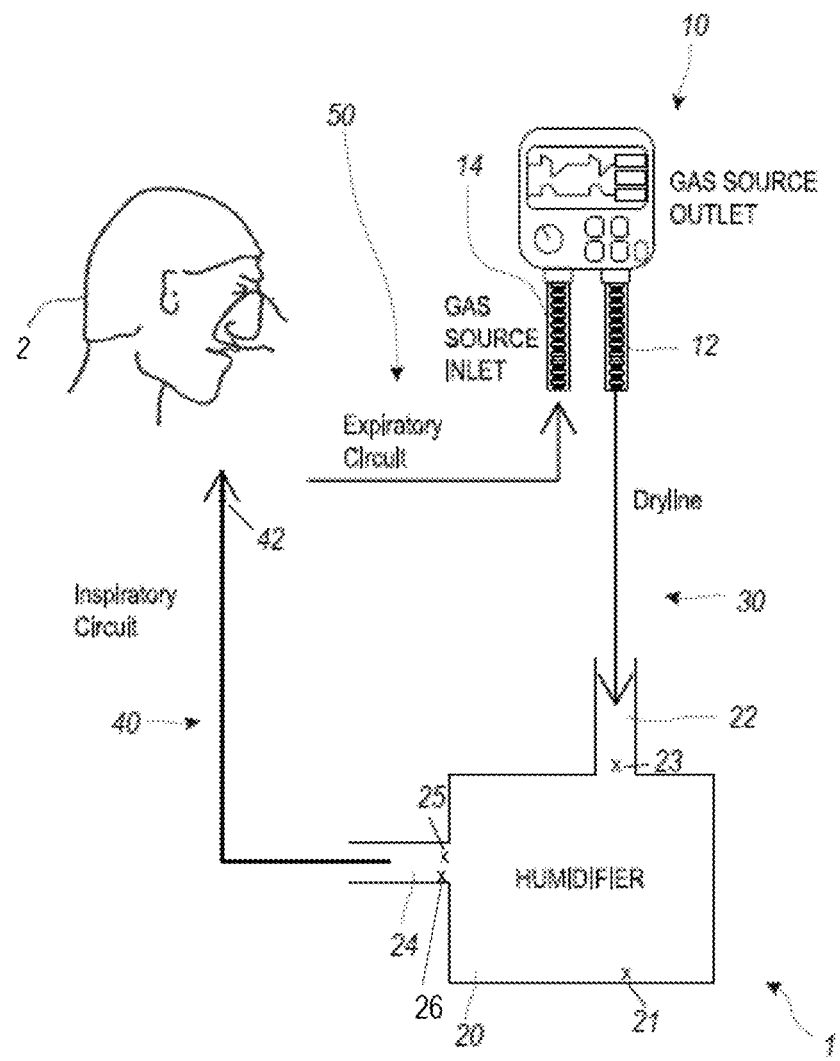
FIG. 5A illustrates a schematic representation of a dual-limb humidification system with various sensors located in the system.

In this disclosure, an inlet temperature is a temperature measured by a humidifier inlet temperature sensor 23 at or near the humidifier inlet 22 as shown in FIG. 5A. An outlet temperature is a temperature measured by a humidifier outlet temperature sensor 25 at or near the humidifier outlet 24. A tube temperature is a patient end temperature measured by a patient end temperature sensor 42 at or near a patient end of the inspiratory conduit 40. The patient end sensor 42 can be integrated into the inspiratory conduit 40 or removably inserted into a gases lumen of the inspiratory conduit 40. A humidifier heat source temperature is the temperature measured by a humidifier heat source temperature sensor 21 at or near the humidifier heat source of the humidifier 20. An outlet set point is a set point temperature that the system tries to achieve at or near the humidifier outlet 24. A tube set point is a set point temperature that the system tries to achieve at or near the patient end of the inspiratory conduit 40. At least one of the humidifier inlet sensor 23, the humidifier outlet sensor 25, and/or the patient end sensor 42 can be a thermistor that can be configured to measure both temperature and flow rate of a gases flow. The system 1 can have a second humidifier outlet sensor 26, which can be a flow rate sensor, a pressure sensor, or any other sensors configured to measure parameters of the gases flow. The system 1 can include additional sensors, for example, other types of flow rate sensors, humidity sensors, or others, at or near the humidifier inlet 22, humidifier outlet 24, and/or patient end of the inspiratory conduit 40. The humidifier inlet 22, humidifier outlet 24, and/or patient end of the inspiratory conduit 40 can each have one or more sensors disclosed herein. The humidification system 1 can also include one or more sensors in other locations of the system.

Temperature-Based Passive & Active Processes

Principles behind the temperature-based passive and active processes will now be described. In normal operation of the system, cold gases flow into the humidifier inlet. The humidifier heat source of the humidifier can be turned on by the controller to warm up the gases, which can leave the humidifier outlet at a higher temperature than the gases flowing into the humidifier inlet. As a result, the inlet temperature can be lower than both the outlet temperature and the outlet set point.

In addition, in normal operation of the system, the gases leaving the humidifier outlet can cool down when traveling through the inspiratory conduit, unless the inspiratory conduit is heated. Therefore, the system can supply power to the inspiratory conduit heat source in the inspiratory conduit to ensure that the tube temperature reaches and remains at the tube set point. There can be a temperature gradient from the humidifier outlet to the patient end of the inspiratory conduit. The gradient is a rising temperature gradient from the humidifier outlet to the patient end of the inspiratory conduit. Accordingly, the tube temperature can be greater than the outlet temperature, but lower than or equal to the tube set point. Alternatively, the temperature gradient from the humidifier outlet to the patient end is not necessarily increasing, but provides enough power so that the temperature of the gas does not drop below the dew point and cause rain out.

The temperature-based reverse flow detection processes can make use of differences in temperature at various locations of the system as described above. If the normal flow temperature differences are not observed, the controller can determine an indication of reverse flow conditions, such as the errors shown in FIGS. 2A-D and 3B. For example, temperature rising from the patient end to the humidifier outlet can indicate that the gases are flowing from the patient end to the humidifier outlet or that the inspiratory conduit is incorrectly connected. Details of the temperature-based passive and active processes will be described with reference to FIGS. 5B-8B.

Passive Process—Inlet Over Temperature Test

A passive process can utilize a relationship of an inlet temperature and the set points of the system. Such a process can be configured for use in a noninvasive (NIV) therapy mode, although the processes can be configured for use in any therapy modes. In the NIV therapy mode, the tube set point can be set at or below normal human body temperature. For example, the tube set point can be a set point in the range of about 25-37° C., 28-35° C., 30-34° C., or any suitable range. As another example, the outlet set point can be a set point in the range of about 22-35° C., 25-33° C., 27-31° C., or any other suitable range. The tube and outlet end set points can correspond with each other. In a non-limiting example, when the tube set point is 34° C., the outlet set point can be about 31° C. As the patient receiving the respiratory therapy in the NIV therapy mode has a body temperature of about 37° C., the exhaled air in this non-limiting example can be at or slightly below 37° C. If a reverse flow condition is present, the exhaled air can be received at the patient end of the inspiratory conduit, leading to a higher tube temperature than the tube set point. The higher tube temperature than the tube set point can occur, for example, in the reverse flow conditions shown in FIGS. 2A and 2C. In a reverse flow situation, the tube temperature can exceed the tube set point for an extended period of time. For example, the humidification system can further determine if the period for which the tube temperature exceeds the tube set point is longer than a predetermined threshold time.

As the tube temperature can be higher than the tube set point in a reverse flow condition, the controller can cause the inspiratory conduit heat source of the inspiratory conduit to have a 0% or very low duty cycle. The gases moving through the inspiratory conduit in the wrong way can cool down because the inspiratory conduit heat source is not heating the gases flowing through the inspiratory conduit. When the cooled gases reach the humidifier outlet, the temperature sensor at the outlet can detect an outlet temperature lower than the outlet set point. This can cause the humidifier heat source to have a first duty cycle to heat up the gases in the humidifier. The first duty cycle can be any duty cycle large enough to cause a change in the temperatures at the humidifier inlet and outlet. The first duty cycle can be the maximum duty cycle or approximately the maximum duty cycle. Duty cycles less than the maximum duty cycle may still change the temperature, however it may take a longer amount of time for the change to be measurable, accordingly other suitable duty cycles can be used. As a result of the application of the first duty cycle, the inlet temperature can exceed both the outlet temperature and set point in a reverse flow condition.

The process can instruct the controller to directly compare the inlet temperature with the outlet temperature in the NIV therapy mode. In normal operation, the inlet temperature is less than the outlet temperature since the humidifier heat source temperature is hot enough that the gases are heated as they travel from the inlet to the outlet. Therefore, if the inlet temperature is higher than the outlet temperature, an indication of reverse flow conditions can be provided to a user.

Figure 5B:
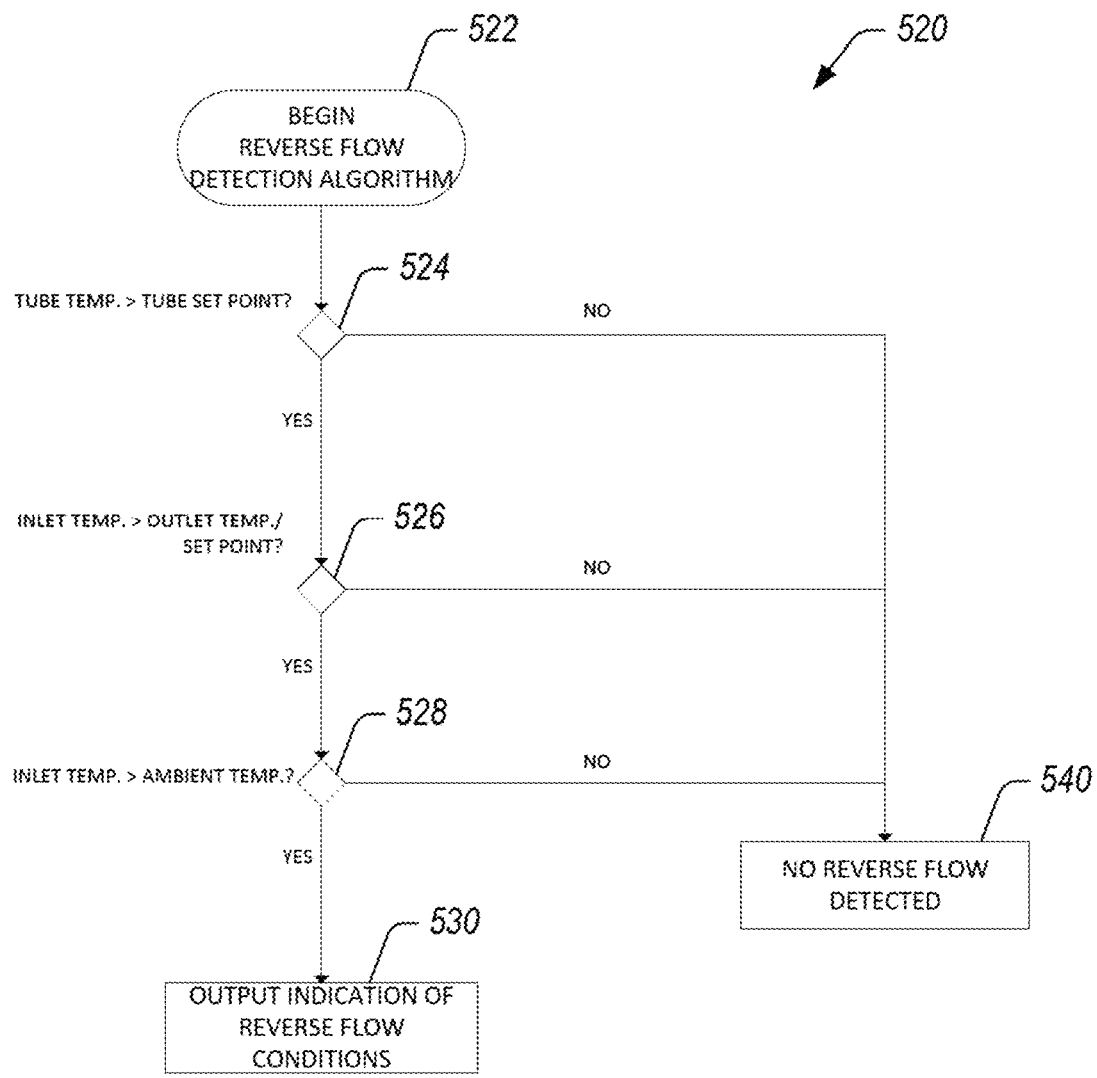
FIG. 5B illustrates a flow chart of an exemplary passive reverse flow detection process.

A multi-step passive process 520 as shown in FIG. 5B can also be implemented. As shown in FIG. 5B, after the controller begins 522 implementing the reverse flow detection process 520, the controller can determine if the tube temperature is higher than the tube set point at step 524. If the tube temperature is lower than the tube set point, the controller can determine that there is no a reverse flow condition at step 540. The system can output an indication that no reverse flow condition is detected, output no indication, and/or either begin a ventilation and/or humidification therapies or continue its current ventilation and/or humidification therapies at step 540. If the tube temperature is higher than the tube set point, which indicates that the inspiratory conduit heat source is not heating up the inspiratory conduit and that the humidifier heat source is likely heating up the gases in the humidifier, the controller can check if the inlet temperature is higher than the outlet temperature or higher than the outlet set point at step 526. In a normal flow condition, the inlet temperature is lower than the outlet temperature because the gases are heated as they leave the humidifier outlet. If the inlet temperature does not exceed either the outlet temperature or the outlet set point, the system can output no indication of reverse flow conditions at the step 540. The system can either begin a respiratory therapy or continue its current respiratory therapy.

With continued reference to FIG. 5B, if the inlet temperature exceeds either the outlet temperature or outlet set point, the system can optionally further determine if the inlet temperature is higher than an ambient temperature at step 528 as additional confirmation that reverse flow conditions are likely present. Specifically, the inlet temperature is approximately equal to or less than the ambient temperature under a forward flow condition because most gases sources supply either ambient air or gases from a gas tank. In either case, it is unlikely that a temperature of the gases supplied by the gases source as indicated by the inlet temperature can exceed the ambient temperature. The ambient temperature can also be measured by an optional ambient sensor, be manually entered by the user, or be received from the gases source.

Either after determining that the inlet temperature is higher than the outlet temperature or set point at the step 526, or after determining that the inlet temperature is also higher than the ambient temperature at the step 528, the controller can output an indication of reverse flow conditions at step 530. The process 520 can check if the inlet temperature is higher than the ambient temperature at the step 528 before checking if the inlet temperature is also higher than the outlet temperature or outlet set point at the step 526. The process 520 can also check if the inlet temperature is higher than both the outlet temperature and set point at the step 526. The process 520 can optionally also check if the inlet temperature is higher than all of the outlet temperature, set point, and ambient temperature in any order. Further, the controller can determine that a reverse flow condition is likely present in the humidifier. The system can alert the user with the methods described herein.

Passive Process—Tube Over Temperature Test

A passive process can also utilize the tube temperature as a reference point. Such a process can be configured for use in an invasive therapy mode or a high flow therapy mode, although the processes can be configured for use in any therapy modes. In the invasive or high flow therapy mode, the tube set point can be at about or higher than the normal human body temperature. In the invasive therapy mode, the tube set point can be about 40° C. and the outlet set point can be about 37° C. In the high flow therapy mode, the tube set point can be about 36-40° C. and the outlet set point can be about 33-37° C. As the patient receiving the respiratory therapy can have a body temperature of about 37° C., the exhaled air can be at or slightly below 37° C. If a reverse flow condition is present, the exhaled air can be received at the patient end of the inspiratory conduit, leading to the tube temperature falling below the tube set point. The lower tube temperature than the tube set point can occur, for example, in the reverse flow conditions shown in FIGS. 2A and 2D.

When the exhaled gases flow from the patient to the humidifier in a reverse flow condition, the inspiratory conduit heat source can heat the gases at up to a first inspiratory conduit heat source duty cycle. The first inspiratory conduit heat source duty cycle can be the maximum duty cycle or approximately the maximum duty cycle. The inspiratory conduit heat source can be activated because the controller is programmed to supply power to the inspiratory conduit heat source if the tube temperature is less than the tube set point. The controller is configured to make the tube temperature reach the set point even in reverse flow conditions because the controller in existing humidification systems is not configured to directly or indirectly detect reverse flow conditions.

Figure 6:
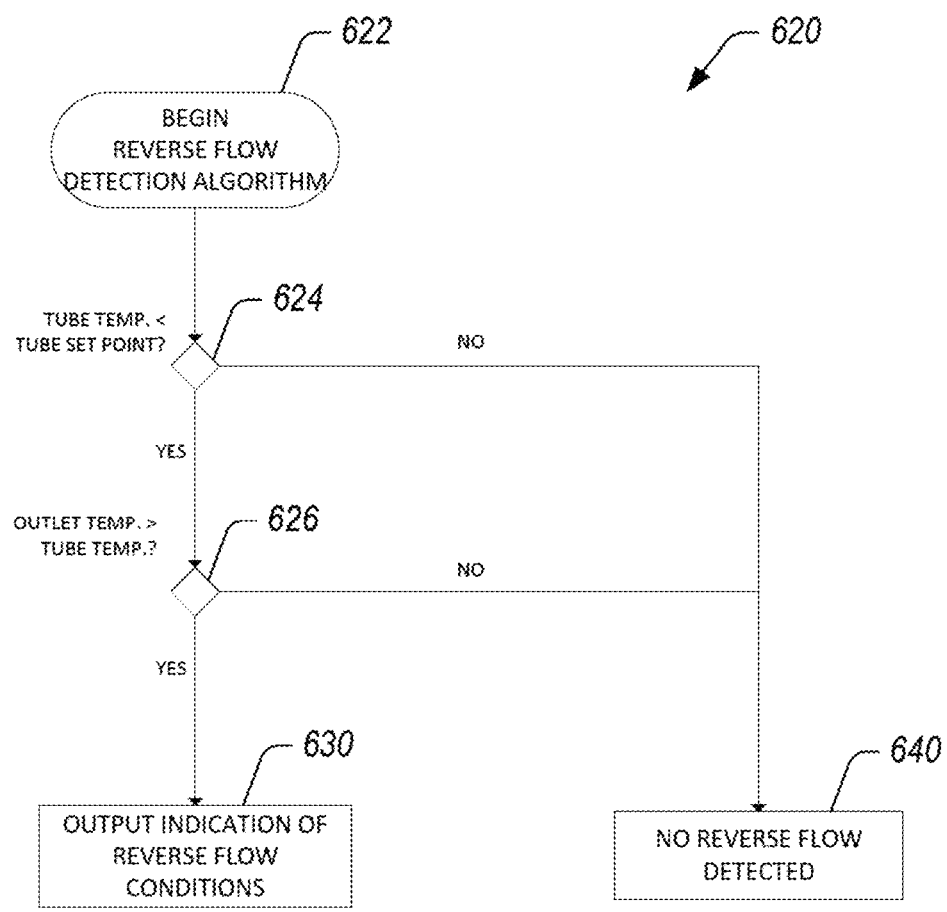
FIG. 6 illustrates a flow chart of another exemplary passive reverse flow detection process.

FIG. 6 illustrates an example passive "tube over temperature" process 620 for detecting an indication of reverse flow conditions using the tube temperature as a reference point. After the controller begins 622 implementing the process 620, the controller can determine if the tube temperature is lower than the tube set point at step 624. A lower tube temperature than the tube set point can be interpreted by the controller as not indicating reverse flow conditions at step 640. The system can output an indication that no reverse flow condition is detected, output no indication, and/or either begin a ventilation and/or humidification therapies or continue its current ventilation and/or humidification therapies at step 640.

If the tube temperature is lower than the tube set point, the controller can check if the outlet temperature is higher than the tube temperature at step 626. Because the tube temperature is lower than the tube set point, the inspiratory conduit heat source can be heating the inspiratory conduit to try to bring the gases traveling in the inspiratory conduit to the tube set point. In a normal flow condition, the gases leaving the humidifier outlet can be at a lower temperature than the gases at the patient end of the inspiratory conduit. The heating gradient can rise from the outlet to the patient end when the inspiratory conduit heat source is turned on. If the outlet temperature is not higher than the tube temperature, the controller can interpret the result as not indicating a reverse condition. The system can output an indication that no reverse flow condition is detected, output no indication, and/or either begin a ventilation and/or humidification therapies or continue its current ventilation and/or humidification therapies at step 640.

With continued reference to FIG. 6, if the tube temperature is lower than the outlet temperature, the controller can output an indication of reverse conditions at step 630. As the colder exhaled air is likely flowing in a reverse direction from the patient end to the humidifier outlet, the controller can determine that the inspiratory conduit has likely been incorrectly connected. The system can alert the user with the methods described herein.

The passive reverse flow detection processes described herein can be advantageous because there is no interruption to the respiratory or ventilation therapy and/or the humidification therapy that the system is providing to the patient, making it more convenient to the patient while still ensuring patient safety by detecting the reverse flow conditions and/or incorrect connections. Running the passive processes in the background requires no additional processing by the controller as there is no need to heat the inspiratory conduit heat source or the humidifier heat source outside the therapy mode. Controls of the inspiratory conduit heat source and the humidifier heat source can function as normal. Further, waiting time is not required for the inspiratory conduit heat source or the humidifier heat source to reach a steady state or a particular temperature before the passive processes can be implemented.

Active Process—High Humidifier Heat Source Duty Cycle (or Power) Test

The passive processes described herein are controller dependent. In order for the passive processes to work, the controller setup of the system needs to be built into the passive processes. The passive processes can be effective when the controller operation can be known, such as when the user presets the controller operations. In contrast, active processes can be independent of controllers such as the humidifier heat source controller, the inspiratory conduit heat source controller, and/or the like. The active processes can be effective when the controller operation is unknown.

Figure 7A:
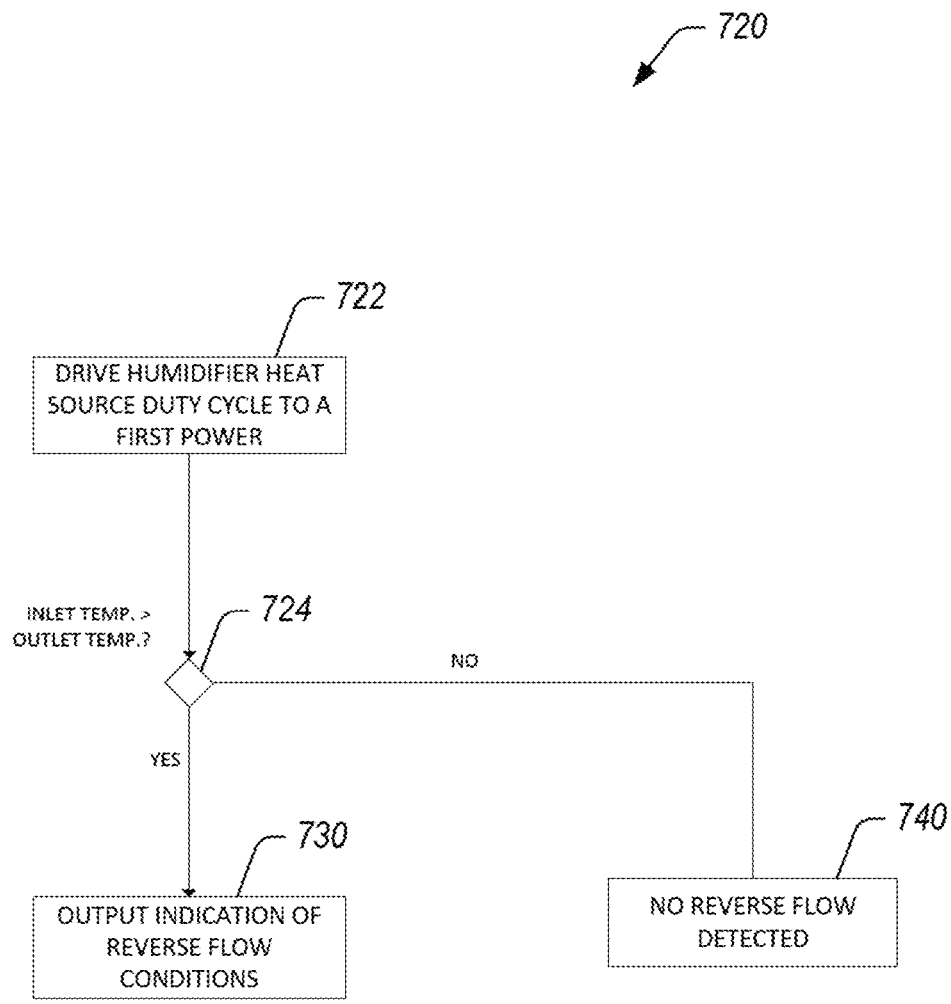
FIGS. 7A-B illustrate flow charts of exemplary active reverse flow detection process.
Figure 7B:
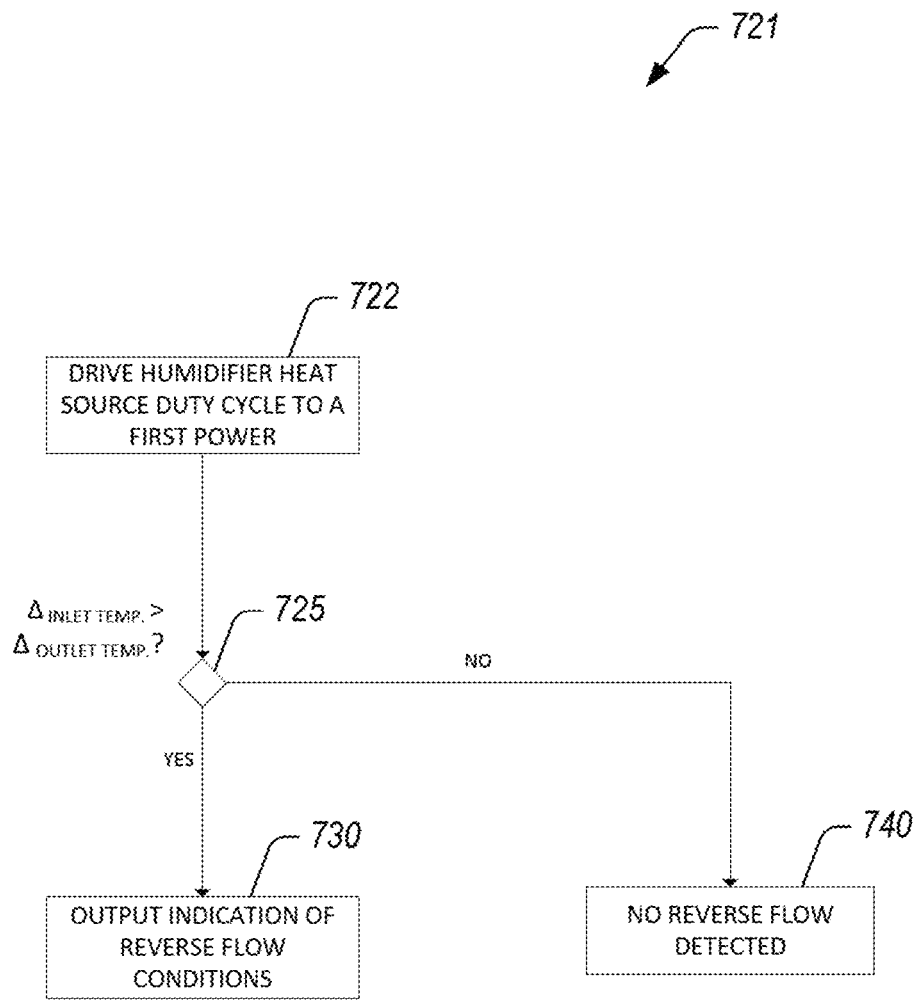

FIGS. 7A-B illustrate example active processes 720, 721. As shown in FIGS. 7A-B, the controller can first actively drive the humidifier heat source duty cycle to a first duty cycle at step 722. The first duty cycle can be about 100%. The active process 720, 721 can advantageously be implemented independent of the humidifier heat source controller. The controller, when implementing the active process 720, 721, can interrupt a therapy that is running in the system. The therapy can be a respiratory or ventilation therapy and/or a humidification therapy. Like in the passive process 500, the outlet temperature is expected to be higher than the inlet temperature in a normal flow condition, because the gases can be heated by the humidifier heat source at the first duty cycle when the gases flow from the humidifier inlet to the humidifier outlet. The first duty cycle is large enough to heat the humidifier heat source to cause temperature changes at the humidifier inlet and outlet. If there is a reverse flow condition, the gases can be heated from the outlet to the inlet instead. As shown in FIG. 7A, the controller can determine at step 724 if the inlet temperature is higher than the outlet temperature. As shown in FIG. 7B, the controller can determine at step 725 if a change in the inlet temperature is higher than a change in the outlet temperature.

If the inlet temperature is lower than the outlet temperature or if the inlet temperature change is less than the outlet temperature change, the controller can interpret the result as not indicating a reverse flow condition at step 740. The system can output an indication that no reverse flow condition is detected, output no indication, and/or either begin a ventilation and/or humidification therapies or continue its current ventilation and/or humidification therapies at step 740. If the inlet temperature is higher than the outlet temperature or if the inlet temperature change is greater than the outlet temperature change, the system can output an indication of reverse flow conditions at step 730. Further, the controller can determine that connections to the humidifier are likely incorrect. The controller can also compare both the absolute temperatures and the changes in the temperatures at the humidifier inlet and outlet in any order. The system can alert the user of the incorrect connections with methods described herein. The system may not resume the interrupted therapy until the user rectifies the reverse flow condition in the system.

Active Process—High Inspiratory Conduit Heat Source Duty Cycle (or Power) Test

Figure 8A:
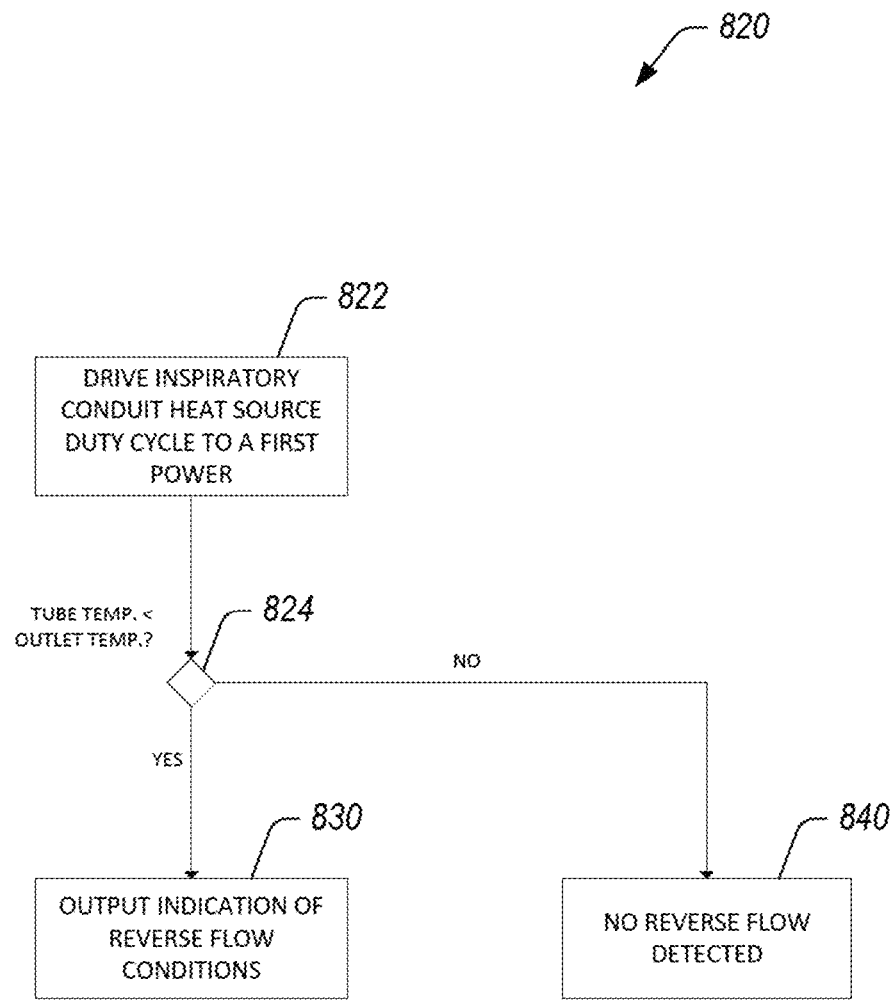
FIGS. 8A-B illustrate flow charts of additional exemplary active reverse flow detection process.
Figure 8B:
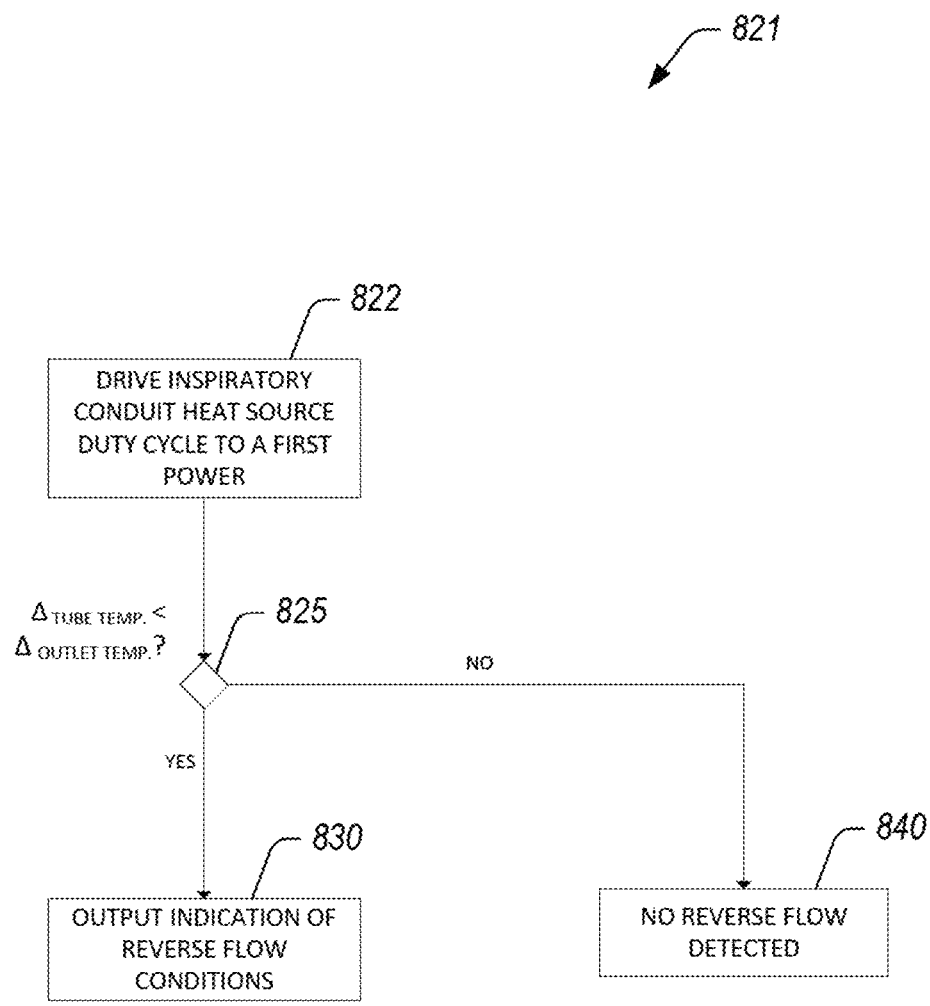

FIGS. 8A-B illustrate example active processes 820, 821. As shown in FIGS. 8A-B, the controller can first actively drive the inspiratory conduit heat source duty cycle to a first duty cycle at step 822. The first duty cycle can be about 100%. The first duty cycle is large enough to heat the inspiratory conduit heat source to cause temperature changes at the humidifier outlet and the patient end of the inspiratory conduit. The active process 820, 821 can advantageously be implemented independent of the inspiratory conduit heat source controller. The controller, when implementing the active process 820, 821, can interrupt a therapy that is running in the system. The therapy can be a respiratory or ventilation therapy and/or a humidification therapy. Like in the passive process 600, the tube temperature is expected to be higher than the outlet temperature in a normal flow condition, because of the heating gradient in the inspiratory conduit. If there is a reverse flow condition, the unheated gases can enter the patient end of the inspiratory conduit and be heated as the gases reach the humidifier outlet, resulting in a lower tube temperature than the outlet temperature. As shown in FIG. 8A, the controller can determine at step 824 if the tube temperature is lower than the outlet temperature. As shown in FIG. 8B, the controller than determine at step 825 if a change in the tube temperature is less than a change in the outlet temperature.

If the tube temperature is higher than the outlet temperature or if the tube temperature change is greater than the outlet temperature change, the controller can interpret the result as not indicating a reverse flow condition at step 840.

The system can output an indication that no reverse flow condition is detected, output no indication, and/or either begin a ventilation and/or humidification therapies or continue its current ventilation and/or humidification therapies at step 840. If the tube temperature is lower than the outlet temperature or if the tube temperature change is less than the outlet temperature change, the system can output an indication of reverse flow conditions at step 830. Further, the controller can determine that connection of the inspiratory conduit is likely incorrect. The controller can also compare both the absolute temperatures and the changes in the temperatures at the patient end and the humidifier outlet in any order. The system can alert the user of the incorrect connections with methods described herein. The system may not resume the interrupted therapy until the user rectifies the reverse flow condition in the system.

In addition to being humidifier heat source/wire controller independent, the active processes 720, 721, 820, 821 can advantageously result in a more easily detectable temperature difference in the steps 724, 725, 824, 825 because the inspiratory conduit heat source or the humidifier heat source is driven to a high heating capacity. The higher heater capacity can be a maximum or substantially maximum duty cycle.

Active Process—Upstream and Downstream Temperature Gradients Test

Figure 9A:
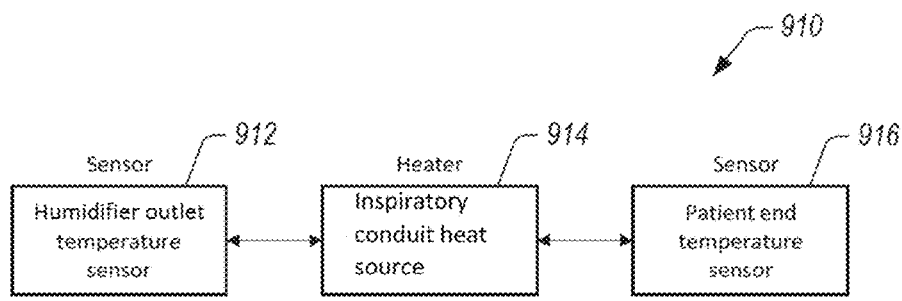
FIGS. 9A-C illustrate components of a humidification system for implementing certain active reverse flow detection processes.
Figure 9B:
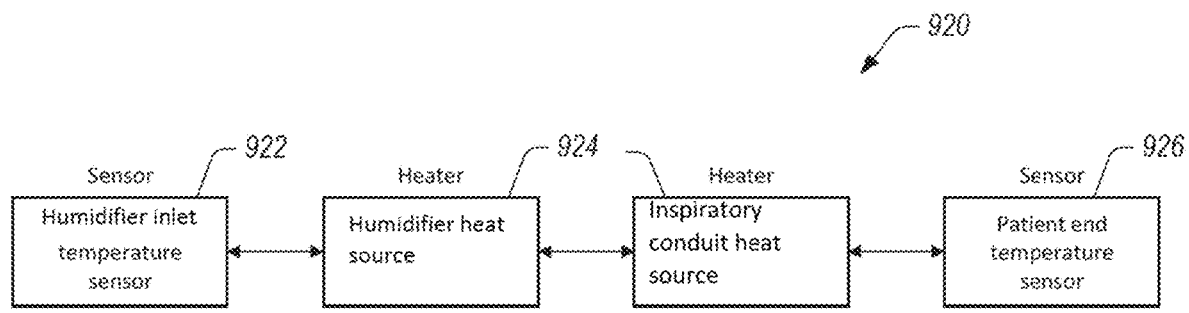
Figure 9C:
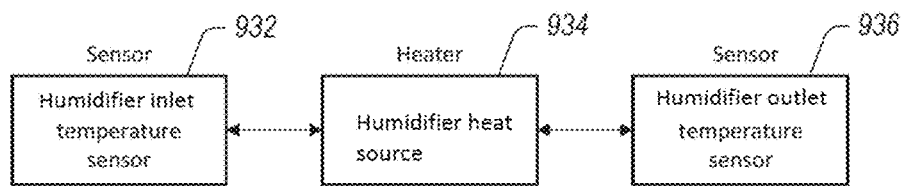

FIGS. 9A-C illustrate combinations 910, 920, 930 of sensors and heaters of a humidification system that can implement active reverse flow detection processes that compare upstream and downstream temperature gradients. The processes can be carried out from an initial "cold" and/or unheated start-up condition. The processes can be carried out after start-up, such as during normal operation of the humidification system, by providing a heating pattern. The temperature gradient at a sensor location can be a rate of change of the temperature sensor measurements. When the heater(s) of the humidification system are heated from an initial unheated condition, the temperature gradient observed at a downstream temperature sensor is expected to be higher than the temperature gradient observed at an upstream temperature sensor in a normal flow condition. This is because in a normal flow condition, the gases flow is heated up as the gases flow from a gases source, through the humidifier and the inspiratory conduit, toward the patient interface.

Various sensors can be the upstream or downstream temperature sensors. The sensors can include the humidifier outlet temperature sensor, the humidifier inlet temperature sensor, and/or the patient end temperature sensor. Various heaters can be heated up for the active processes. The heaters can include the humidifier heat source and/or the inspiratory conduit heat source. As shown in FIG. 9A, the active process can utilize the combination 910 comprising the humidifier outlet temperature sensor as the upstream sensor 912, the inspiratory conduit heat source as the heater 914, and the patient end temperature sensor as the downstream sensor 916. The humidifier heat source can be deactivated. As shown in FIG. 9B, the active process can utilize the combination 920 comprising the humidifier inlet temperature sensor as the upstream sensor 922, the humidifier heat source and the inspiratory conduit heat source as the heater 924, and the patient end temperature sensor as the downstream sensor 926. As shown in FIG. 9C, the active process can utilize the combination 930 comprising the humidifier inlet temperature sensor as the upstream sensor 932, the humidifier heat source as the heater 934, and the humidifier outlet temperature sensor as the downstream sensor 936. The inspiratory conduit heat source can be deactivated.

Figure 10:
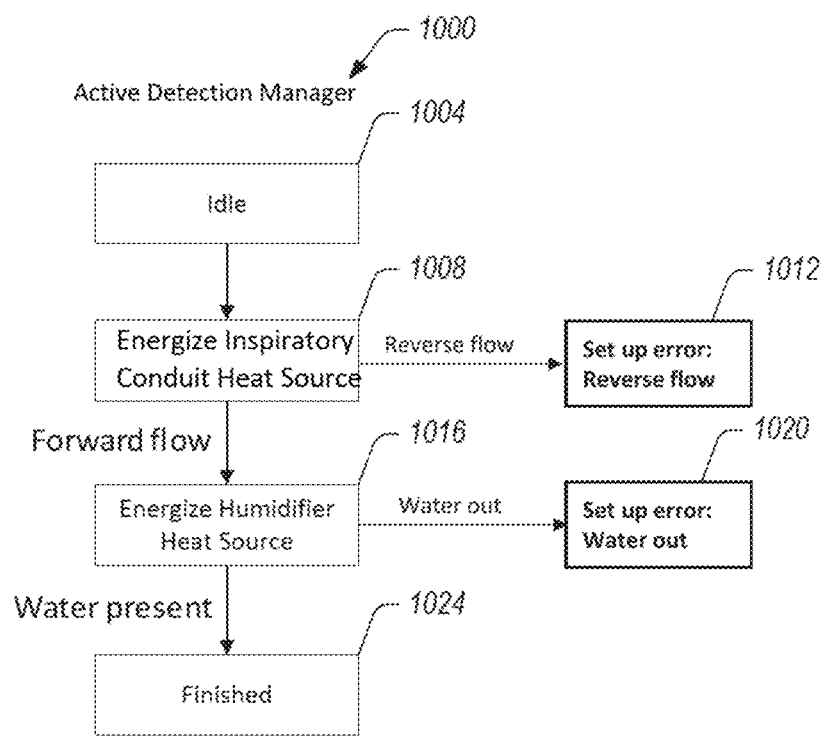
FIG. 10 illustrates a flow chart of exemplary active reverse flow and water-out detection processes.
Figure 11A:
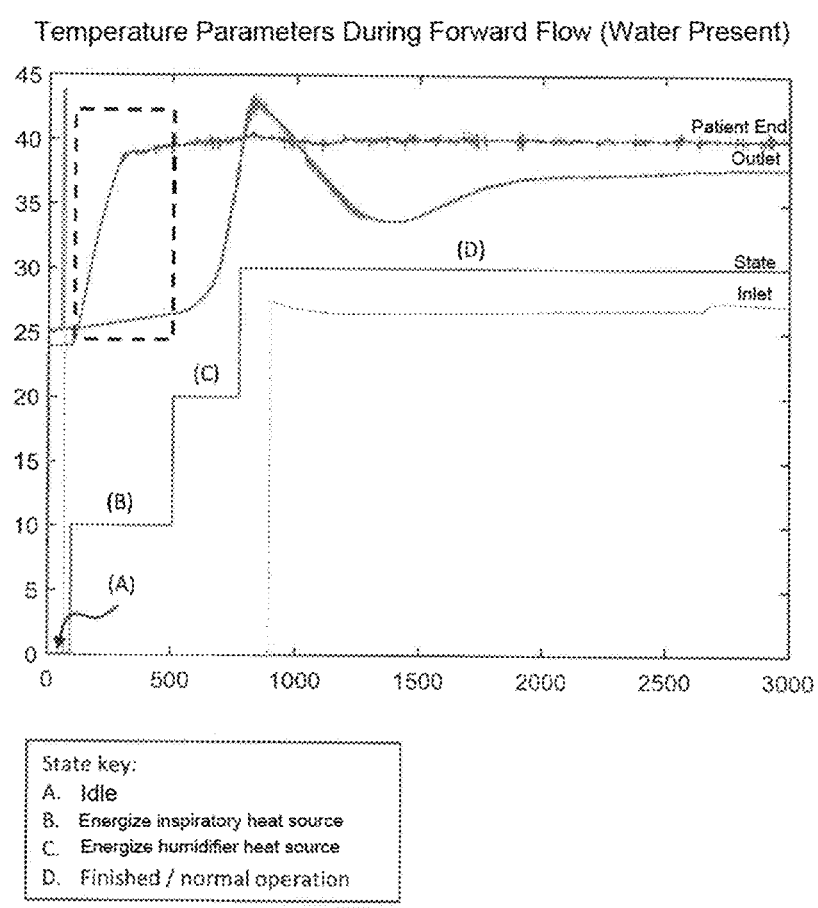
FIGS. 11A-D illustrate exemplary system temperature parameters of a humidification system upon implementing the processes of FIG. 10 under forward flow and reverse flow conditions, respectively.
Figure 11B:
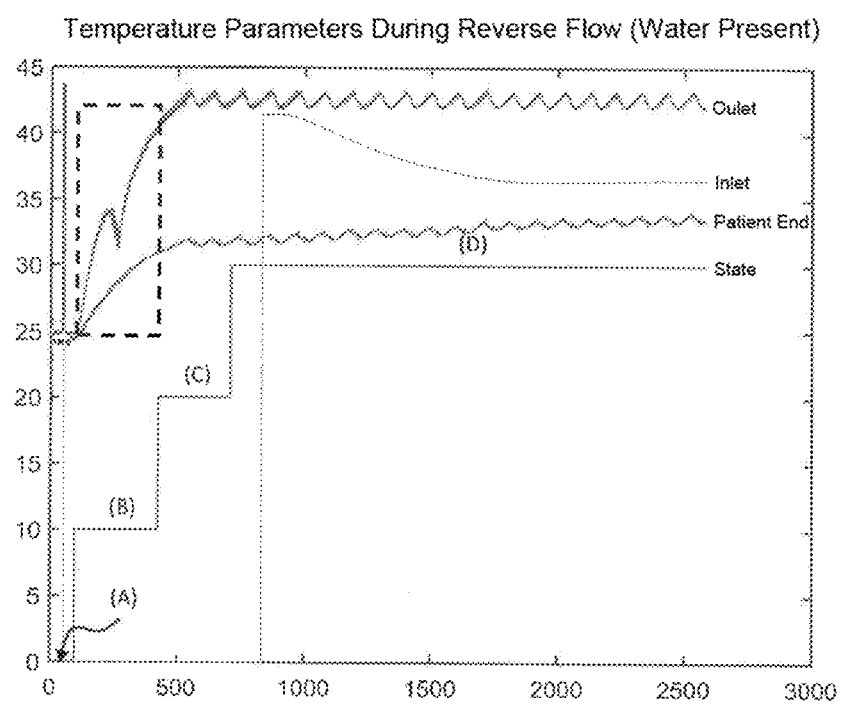
Figure 11C:
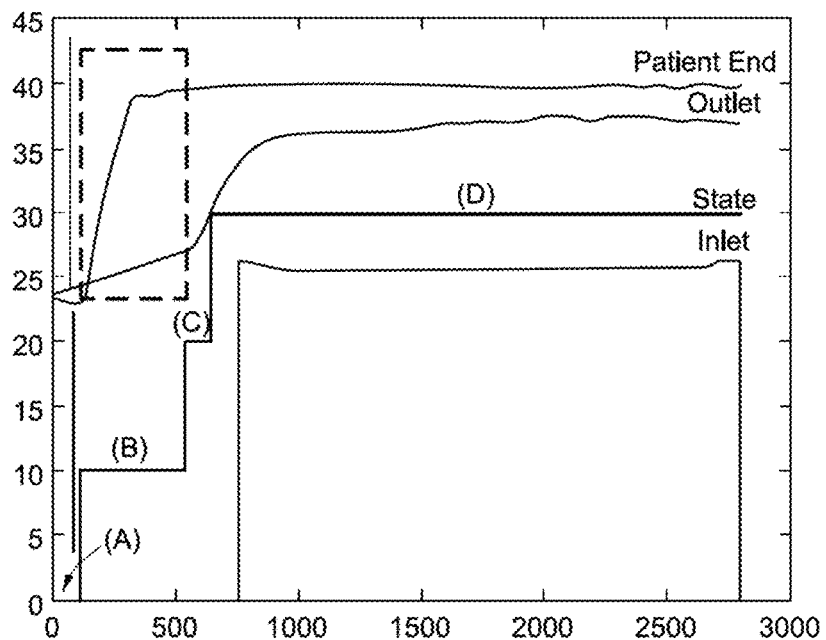
Figure 11D:
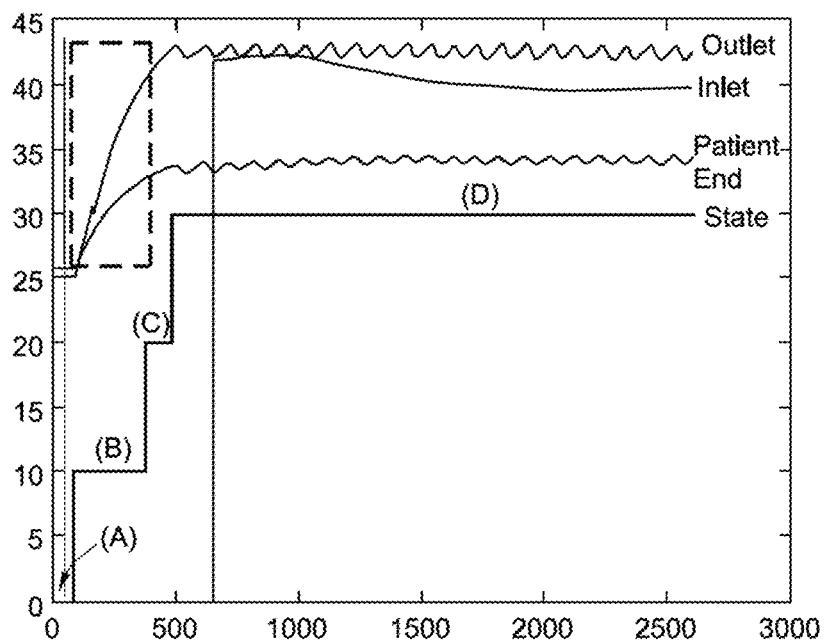

FIG. 10 illustrates an example active-detection manager 1000 that utilizes the combinations 910 of FIG. 10A. The humidifier outlet temperature sensor for detecting the humidifier outlet temperature can be the upstream sensor. The patient end temperature sensor for detecting the patient end temperature can be the downstream sensor. The active-detection manager 1000 can utilize other combinations, such as the combinations 920, 930 of FIGS. 10B and 10C.

In step 1004, the active-detection manager 1000 can be in an idle state. In the idle state, the active-detection manager 1000 can be waiting for completion of a system self-test. The system self-test can check for hardware disconnection and/or fault, and/or comprise the probe-out test. Some sensors may not be available during the self-test. For example, the flow sensors may need to be warmed up before the sensors can be available for detecting a flow rate. The controller may not be able to perform heating control during the self-test. The active-detection manager 1000 can also be waiting for a flow of gases to be detected in the step 1004.

After completion of the self-test, the active-detection manager 1000 can energize the inspiratory conduit heat source in the inspiratory conduit in step 1008. The active-detection manager 1000 can provide a 100% duty cycle or a power until the tube temperature detected by the patient end temperature sensor reaches a preset threshold temperature or maximum limit, either once or for a predetermined duration. The power can be a constant power, or at a variable power with a known pattern, which can be a pattern of pulses or a waveform or the like. The maximum limit can be about 40° C. The humidifier heat source can be deactivated. The active-detection manager 1000 can stop energizing the inspiratory conduit heat source if the tube temperature or the humidifier heat source temperature exceeds a threshold. The threshold can be a safety maximum temperature limit. The tube or humidifier heat source temperature can exceed a threshold due to a warm start, or due to temporary disconnection of the inspiratory conduit from the humidifier. A warm start can occur by starting the system when the system has not cooled down to an ambient temperature.

Figure 12A:
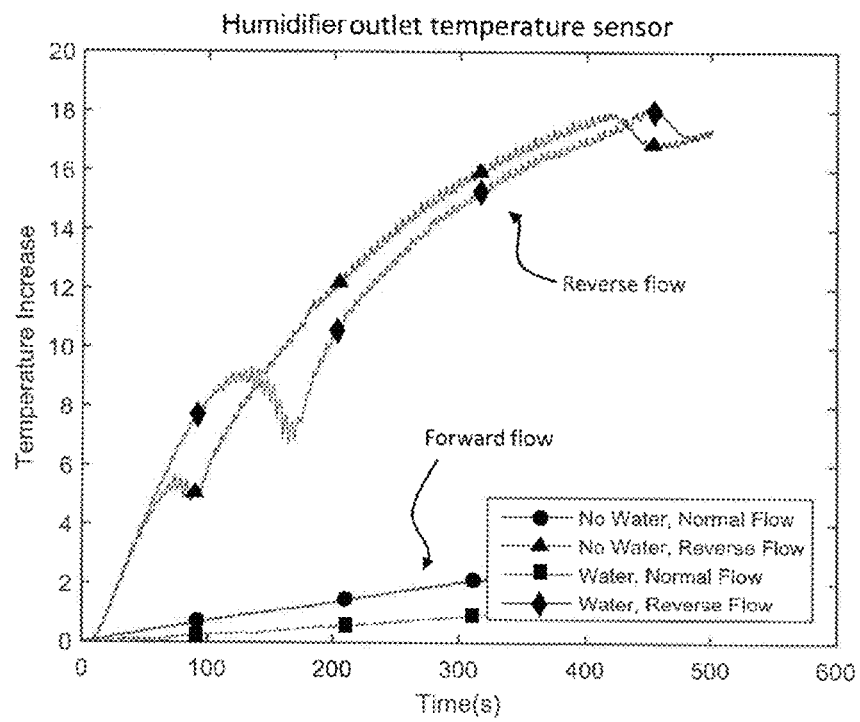
FIG. 12A illustrates exemplary temperature changes detected by a humidifier outlet temperature sensor of a humidification system after activation of an inspiratory conduit heat source in an inspiratory tube when implementing the processes of FIG. 10.
Figure 12B:
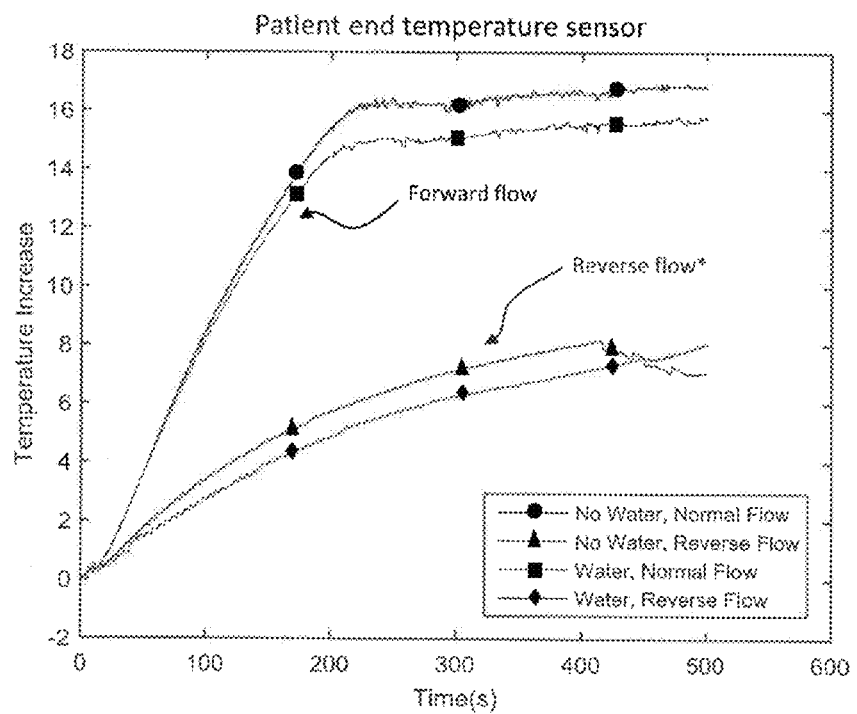
FIG. 12B illustrates exemplary temperature changes detected by a patient end temperature sensor of a humidification system after activation of an inspiratory conduit heat source in an inspiratory tube when implementing the processes of FIG. 10.

The active-detection manager 1000 can monitor and compare the temperature gradients measured by the patient end temperature sensor and the humidifier outlet temperature sensor in the step 1008. As shown in FIGS. 12A and 12B, which illustrate regions enclosed by dash lines in FIGS. 11A-11D, the temperature gradient detected at the patient end is greater than at the humidifier outlet when the gases flow is in the forward direction for some amount of time after activing the inspiratory conduit heat source. In the example illustrated in the figures, this amount of time is approximately 200 seconds, however it should be appreciated by one of skill in the art that this amount of time is dependent on many factors, such as ambient temperature conditions, flow rate, and power supplied to the inspiratory conduit heat source. The amount of time may be a time in the range of about 5 seconds to 10 minutes, 10 seconds to 4 minutes, 10 seconds to 3 minutes, 10 seconds to 200 seconds, 10 seconds to 100 seconds, and/or 50 seconds to 100 seconds. At the humidifier outlet, the gases are not heated because the humidifier heat source is deactivated. At the patient end of the inspiratory conduit, the gases can be heated because the inspiratory conduit heat source is energized under normal flow. The inspiratory conduit heat source can be energized to the maximum duty cycle or a constant power, or at a variable power with a known pattern, which can be a pattern of pulses or a waveform or the like.

As shown in FIGS. 12A-12B, the temperature gradient detected at the humidifier outlet is greater than at the patient end when the gases flow is in the reverse direction for some amount of time after activating the inspiratory conduit heat source. In the example illustrated in the figures, this amount of time is approximately 200 seconds, however it should be appreciated by one of skill in the art that this amount of time is dependent on many factors, such as ambient temperature conditions, flow rate, and power supplied to the inspiratory conduit heat source. The amount of time may be a time in the range of about 5 seconds to 10 minutes, 10 seconds to 4 minutes, 10 seconds to 3 minutes, 10 seconds to 200 seconds, 10 seconds to 100 seconds, and/or 50 seconds to 100 seconds. Gases arriving at the humidifier outlet have been heated by the inspiratory conduit heat source, causing temperature to rise quickly at the humidifier outlet. Gases arriving at the patient end of the inspiratory conduit can be unheated. A temperature gradient at the patient end can be present due to a flow of exhales gases from the heated expiratory conduit traveling into heated inspiratory conduit. The temperature gradients at the patient end and the humidifier outlet can have similar trends when the humidifier has water, or when the humidifier is in a water-out condition.

As described above, the active-detection manager 1000 can energize different heaters to detect reverse flow conditions. The active-detection manager 1000 can energize the humidifier heat source or the combination of the humidifier heat source and the inspiratory conduit heat source in the step 1008. The active-detection manager 1000 can monitor temperature gradients detected by different temperature sensors. The humidifier inlet temperature sensor can be the upstream sensor and the patient end temperature sensor or the humidifier outlet temperature sensor can be the downstream sensor.

When the start-up manger 1000 detects a reverse flow condition based on differences in the temperature gradients of upstream and downstream temperature sensors as described above, the active-detection manager 1000 can output a setup error of reverse flow in step 1012. The output of reverse flow error can trigger an alarm message. The message can be in the form of a video, text, pictorial, or a combination thereof. The message can contain instructions for corrective actions. The active-detection manager 1000 can stop energizing the inspiratory conduit heat source or other activated heaters upon detecting the error.

When the start-up manger 1000 determines that the gases flow is in a forward direction, the active-detection manager 1000 can proceed to step 1016. In step 1016, the active-detection manager 1000 can energize the humidifier heat source to detect a water-out condition. The water-out condition can indicate that the humidifier is empty (zero water level) or when the water level in the humidifier is below a minimum threshold. The minimum threshold can be any suitable threshold, such as in the range of below about 10 mm, 9 mm, 8, mm, 7, mm, 6, mm, 5 mm, 4 mm, 3 mm, 2 mm, and/or 1 mm. The threshold can change based at least in part on flow rate, type of humidifier, any other system parameters, and/or any other ambient conditions. The active-detection manager 1000 can energize the humidifier heat source for a set period of time or to a set point temperature. The humidifier heat source can be energized at a constant power, or at a variable power with a known pattern, which can be a pattern of pulses or a waveform or the like. The constant or variable power can be any suitable power, and it will be appreciated by one of skill in the art that a high power will yield faster results, but with a potential risk for overheating, while a lower power may yield slower results, with lowered risk of overheating, but which may be more susceptible to being affected by the ambient conditions. The constant or variable power may be a power in the range of about 10-250 W, 50-200 W, 25-175 W, 50-150 W, 75-125 W, 100 W and/or 150 W. The active-detection manager 1000 can stop energizing the humidifier heat source if the humidifier heat source exceeds a threshold. The threshold can be a safety maximum temperature limit. In the step 1016, the active-detection manager 1000 can energize the humidifier heat source, or both the humidifier heat source and the inspiratory conduit heat source. When energizing both the inspiratory conduit heat source and the humidifier heat source, a constant power or a variable power with a known pattern can be supplied to the humidifier heat source, as discussed above.

Figure 13:
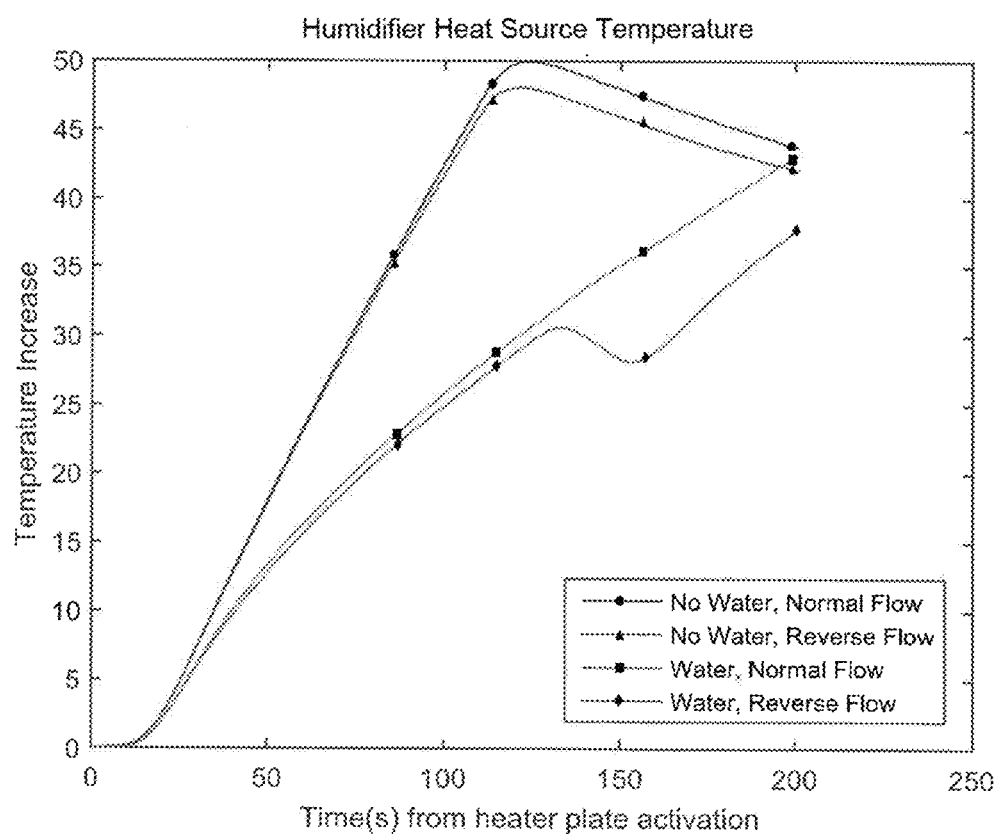
FIG. 13 illustrates exemplary humidifier heat source temperature changes of a humidification system after activation of the humidifier heat source when implementing the processes of FIG. 10.

The active-detection manager 1000 can monitor a temperature gradient at the humidifier heat source at the step 1016. As shown in FIG. 13, the temperature gradient at the humidifier heat source is greater when the humidifier is in a water-out condition than when the water level of the humidifier is greater than zero or a minimum threshold for some amount of time after activation of the humidifier heat source. In the example illustrated in the figure, this amount of time is approximately 150 seconds, however it should be appreciated by one of skill in the art that this amount of time is dependent on many factors, such as ambient temperature conditions, flow rate, and power supplied to the inspiratory conduit heat source. The amount of time may be a time in the range of about 5 seconds to 10 minutes, 10 seconds to 4 minutes, 10 seconds to 3 minutes, 10 seconds to 200 seconds, 10 seconds to 100 seconds, 50 seconds to 150 seconds, and/or 50 seconds to 100 seconds. Under both the forward and reverse flow conditions, the temperature gradient at the humidifier heat source can be higher when the humidifier is in a water-out condition than when the humidifier is not in a water-out condition. Temperature of the humidifier heat source can rise more quickly when there is insufficient water to act as a heat sink to absorb heat from the humidifier heat source. The active-detection manager 1000 can compare the temperature gradient at the humidifier heat source with a predetermined threshold temperature gradient. The humidifier can be in a water-out condition if the temperature gradient exceeds the threshold.

When the start-up manger 1000 detects a water-out condition as described above, the active-detection manager 1000 can output a setup error of water-out in step 1020. The output of water-out error can trigger an alarm message. The message can be in the form of a video, text, pictorial, or a combination thereof. The message can contain instructions for corrective actions. The active-detection manager 1000 can stop energizing the humidifier heat source or other activated heaters upon detecting the error.

When the start-up manger 1000 determines that the humidifier contains water or the water level in the humidifier is above the minimum threshold, the active-detection manager 1000 can proceed to step 1024. In step 1024, the active-detection manager 1000 can be exited and the controller can begin normal operation of the humidification system, Running the active-detection manager 1000 of the humidification system can facilitate detection a reverse flow condition, detection of water running out in the humidifier, and/or minimizing condensate in unheated portions of the inspiratory tube. The active-detection manager 1000 can have independent and predictable control of the humidifier heat source and/or inspiratory conduit heat source on start-up to help with fault detection.

Power Dissipation and/or Flow Rate-Based Passive Processes

Figure 14:
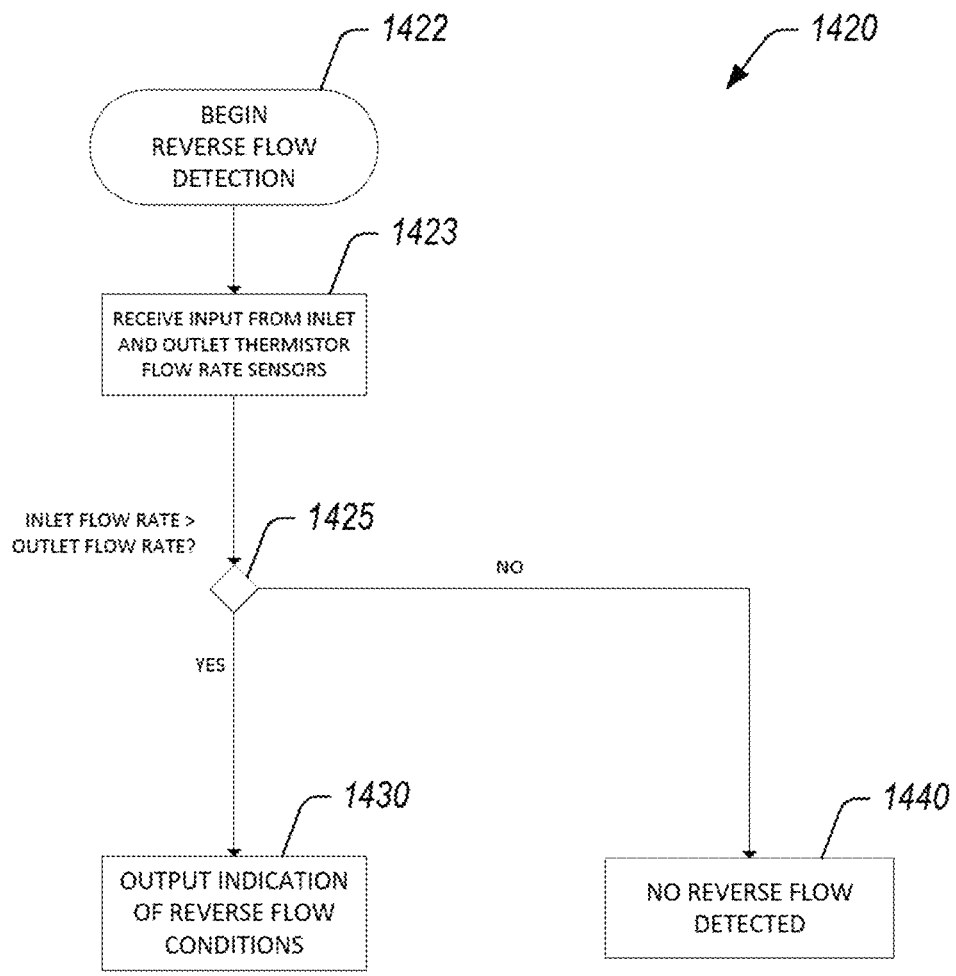
FIG. 14 illustrates a flow chart of another exemplary passive reverse flow detection process.

Reverse flow conditions can be detected based on parameters other than temperature. For example, FIG. 14 illustrates a passive reverse flow detection process 1420 based on flow rate measurements. As described above, the humidification system can include a thermistor at the humidifier inlet and/or outlet. After beginning 1422 a reverse flow detection process, the controller can cause the thermistor to function as a flow rate sensor by first applying a voltage to the thermistor to heat up the thermistor and indirectly measuring the flow rate based on the power dissipation of the thermistor. The controller can receive determined flow rate inputs from the thermistor flow rate sensors at the humidifier inlet and outlet at step 1423. The humidification systems may not be able to directly detect a reverse flow condition because these thermistor flow rate sensors are omni-directional flow sensors. There can also be a dedicated directional-specific and/or non-directional flow sensors, either of which may not require heating at the humidifier inlet and/or outlet. The reverse flow condition can be detected by monitoring changes in the flow rate measurements at different locations of the system. The different locations can include, for example, at or near the humidifier inlet and outlet. The flow rate measurements can vary throughout the system and deviate from a flow rate set point of the system due to the different geometries.

As shown in FIG. 14, the controller can compare the measured inlet flow rate and the outlet flow rate at step 1425. For example, waveforms of flow at the humidifier inlet and the humidifier outlet can be compared. In normal operation of the system, the measured flow rate is higher at the humidifier outlet than at the humidifier inlet. This is because the shape of the humidifier outlet can act as a nozzle and the shape of the humidifier inlet can act as a diffuser for the gases when they flow in the correct direction. As a result, the gases can move through a diffuser at the humidifier inlet and the gases can move through a nozzle at the humidifier outlet. The shape differences of the humidifier inlet and outlet can cause changes in a velocity of the gases, with a lower velocity at the humidifier inlet and a higher velocity at the humidifier outlet. If the inlet flow rate is lower than the outlet flow rate, the controller can interpret the result as not indicating reverse flow conditions at step 1440. The system can output an indication that no reverse flow condition is detected, output no indication, and/or either begin a ventilation and/or humidification therapies or continue its current ventilation and/or humidification therapies at step 1440. If a reverse flow condition is present, such as shown in FIGS. 2A-C and 3B, the flow rate at the humidifier outlet can be lower than the flow rate at the humidifier inlet. The system can output an indication of reverse flow conditions at step 1430. The system can also output an indication that connections to the humidifier are likely incorrect at step 1430. The system can stop the therapy at step 1430. The system can alert the user of the incorrect conditions with methods described herein. The system may not resume the interrupted therapy or start a new therapy until the user rectifies the reverse flow condition in the system.

As another example, the controller can compare power dissipation curves of the thermistor flow rate sensors at the humidifier inlet and the humidifier outlet at the step 1425. Like in the flow rate-based process 1420, the controller needs to first apply a voltage to heat up the thermistor. The power dissipation method can be dependent on the type of gases source, and may require identifying phases of breath and comparing those phases of the power dissipation values at the humidifier inlet and outlet separately. For example, a higher value on the waveform can identify an expiratory phase and a lower value can identify an inspiratory phase. The power dissipation across the outlet sensor can be lower than across the inlet sensor in a normal flow condition because the gases have been heated by the humidifier heat source when they leave the humidifier outlet. The power dissipation across the outlet sensor can be higher in a reverse flow condition because cold gases can be moving across the outlet sensor, as compared to the inlet sensor. Additional details of using the power dissipation curves at the humidifier inlet and outlet for detecting a reverse flow condition are described in U.S. Provisional Application No. 62/362,709.

The controller can also compare both the flow rates and the power dissipations at the humidifier inlet and outlet in any order. One of the reverse flow detection process can be used to cross-check accuracy of another reverse flow detection process.

The flow rate sensors can be calibrated with a zero point reference before the reverse flow detection process 1420. The flow rate sensors can be calibrated to a zero reading when there is no gases flow. The humidification system can have no gases flow when a port cap is still placed on the humidifier inlet, or when a user covers up at least the inlet port of the humidifier when instructed by the humidifier system to calibrate the flow rate sensor. Alternatively, a user or port cap may cover both the inlet and outlet. A user may also cover one or more ports with their hands. The system can provide instructions on calibration with a prompt on a display screen.

Some humidification systems can comprise one or more directional flow sensors to directly detect a reverse flow condition. Detection of a reverse flow condition by the one or more directional flow sensors can prompt the humidification systems to output a warning of possible incorrect connections. The possible incorrect connections can include when the humidification humidifier inlet and outlet have been swapped or mixed up during the setup of the humidification system, or when the ventilator inlet and outlet have been swapped or mixed up during the setup of the humidification system. Although the directional sensor(s) can indicate whether the gas is flowing in the reverse direction from the preferred direction, the sensor(s) may not indicate whether any conduits have been incorrectly attached such as in FIGS. 2B and 2D.

Passive Process Using Sensor Measurements and/or System Parameters

The reverse flow condition detection processes described above can be configured to be run when the humidification system has reached a steady state. A humidification system can be in a steady state when readings from one or more sensors in the humidification system have substantially stabilized. Passive processes can also be implemented during transient states before the readings from the one or more sensors have substantially stabilized. Although the examples described below are described in connection with transient sensor measurements and/or other parameters, the processes described below can also be applied to steady state sensor measurements and/or other parameters for detecting reverse flow conditions.

During the transient states, the sensor inputs can be increasing, decreasing, and/or fluctuating. The system parameters that are monitored can include raw values, raw sensor data, and/or derived or derivative values. The raw values can include heating power, sensor measurements, mode of therapy, and/or others. The heating power can be, for example, of the humidifier heat source, and/or of various portions of inspiratory conduit heat sources such as HW1 and HW2, which are explained below. The sensor measurements can be, for example, inlet temperature, humidifier heat source temperature, outlet temperature, tube temperature, flow rate, and/or filtered or unfiltered flow rate. The humidifier and/or respiratory mode of therapy can include, for example, invasive, mask, noninvasive, high flow, Optiflow™, neonatal, anesthesia, or other modes of therapy. The derived or derivative values can include error between measured value and set-point value, filtered or unfiltered values, differences between parameter values, ratios between parameters, Boolean conditions, gradients and/or integrals, mathematical functions, and/or combinations thereof. The set-point values can include, for example, humidifier heat source set point, outlet set point, or tube set point. The differences between parameter values can include, for example, difference between readings of two temperature and/or flow rate sensors. The ratios between parameters can include, for example, ratios between readings of different sensors. The Boolean conditions can include, for example, whether a parameter is above or below a threshold. The gradients and/or integrals can include, for example, monitoring parameter data in a recent past. Mathematical functions can include, for example, exponents of parameter values.

The controller of the humidification system can also optionally observe various system parameters that are moving towards a steady state. The controller can predict what the steady state values can be. The prediction can be performed using a model for predicting a trajectory of the parameters or other modes of predictions. The controller can run one or more of the passive reverse flow detection processes described above on the predicted steady state values to predict likelihood of a reverse flow condition.

The controller can also optionally first detect whether external conditions have stabilized. An example of the external conditions can include the gases flow. The controller can run a passive transient reverse flow detection process by looking for patterns in the changing and/or unstable system parameters. The system parameters can be one or more of the parameters described above. The controller can use different algorithms for different therapy modes, different flow ranges, and/or other parameters. The humidification system can comprise memory storing look-up tables containing sets of known behavior that can distinguish reverse flow and forward flow conditions. The controller can be configured to determine whether the current conditions are closer to the reverse flow or forward flow behaviors in the table. The controller can interpolate based on the table for conditions not present in the table. The controller can predict a likelihood that a reverse flow condition exists.

The table below provides example parameters at steady state under reverse flow and forward flow conditions, and indicates that these example parameters may be useful in an algorithm for identifying reverse flow or setup error conditions. This is because the differences between the steady state values in reverse and forward flow conditions are large enough to suggest with reasonable confidence that they are not wholly caused by normal measurement error, therapy conditions, flow rate, and/or ambient conditions, but instead are likely due to some setup error and/or reverse flow condition.

| Parameter | Reverse Flow | Forward Flow |
|---|---|---|
| Inlet Temperature (° C.) | 43.07 | 23.30 |
| Outlet Temperature (° C.) | 37.4 | 35.2 |
| Absolute Error (\|Measured Value − Set-point\|) (° C.) | 6.47 | 0.04 |
| Inlet Temperature/Outlet Temperature | 1.01 | 0.68 |
| Inspiratory conduit heat source Power/ Humidifier heat source Temperature | 0.71 | 0.01 |

Figure 15A:
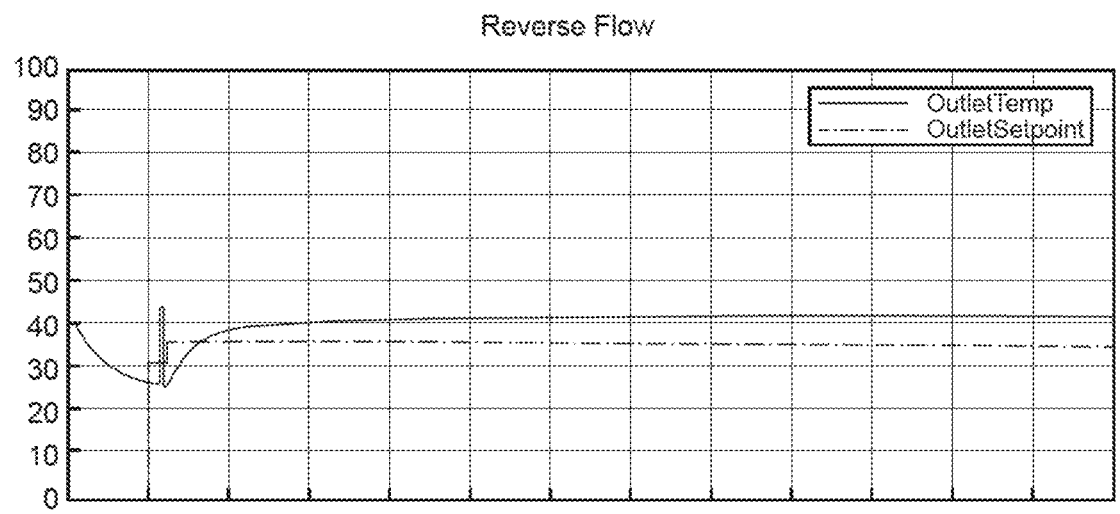
FIGS. 15A-B illustrate example outlet temperature changes under reverse and forward flow conditions, respectively.
Figure 15B:
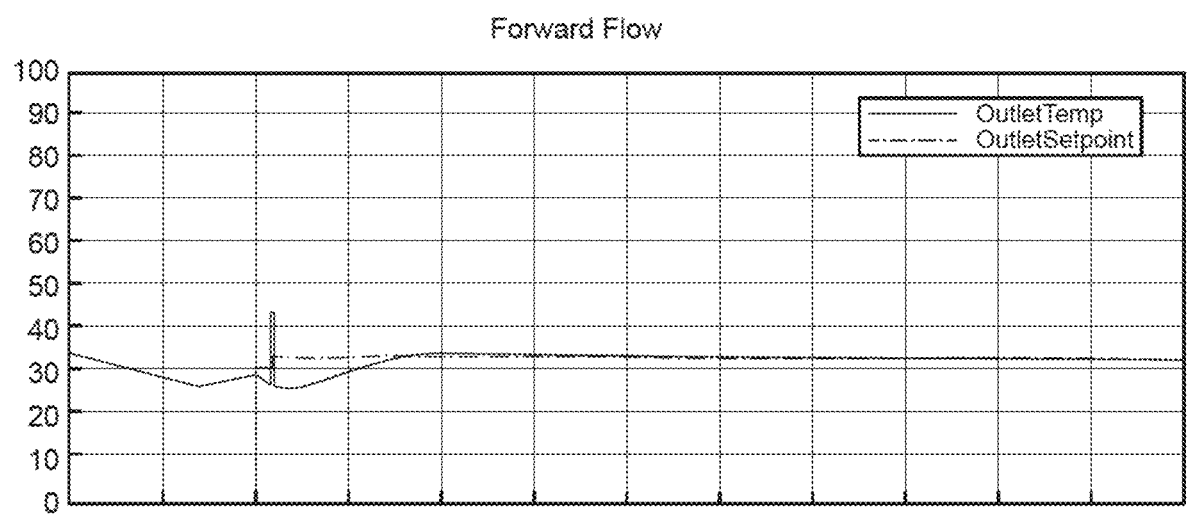

FIGS. 15A-15B illustrate an example of patterns in the changing and/or unstable system parameters. As shown in FIGS. 15A and 15B, temperature at the humidifier outlet approaches and eventually reaches the outlet set-point temperature in forward flow. The temperature at the humidifier outlet does not reach or approach the outlet set-point temperature in reverse flow. This can be due to the gas coming from a different source than expected. For example the tube temperature can be below its set-point temperature if the gas is coming from the gas source or the patient's exhalation instead of from the humidifier during reverse flow. This can also be due to the gas getting heated by a heater that is downstream from the sensor instead of upstream resulting in a temperature that can be higher or lower than the set-point temperature, for example an upstream temperature can be higher than set-point since the gas is getting heated by the inspiratory conduit heat source during reverse flow.

If the system detects a reverse flow condition based on the patterns of unstable parameters, the system can output a reverse flow error alarm in manners described above. The controller can be configured to check for sudden change in the flow rate when a reverse flow condition is detected and/or a reverse flow error alarm is active. The controller can disable the alarm if the external conditions of the system become unstable. For example, the controller can disable the alarm if a sudden flow change is detected. The controller can optionally wait for the flow and/or other unstable external conditions to stabilize. The controller can resume the passive reverse flow detection processes described above.

Figure 16:
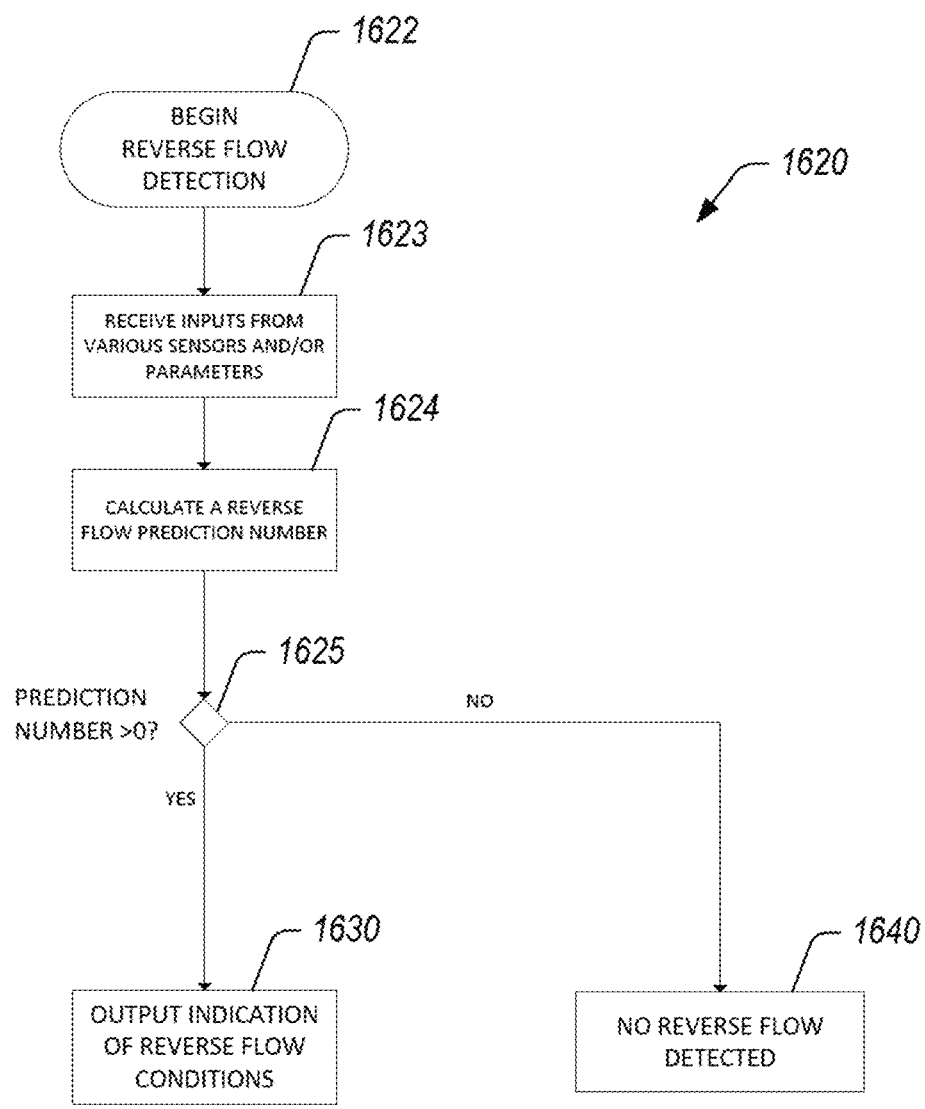
FIG. 16 illustrates a flow chart of an exemplary passive reverse flow detection process.

FIG. 16 illustrates an example passive reverse flow detection process 1620 based on one or more detected parameters during transient states. After beginning 1622 a reverse flow detection process, the controller can receive transient state inputs from various sensors and/or system parameters described herein at step 1623. Examples of the parameters monitored can include, for example, a humidifier inlet temperature, a humidifier outlet temperature, a humidifier outlet set point, a flow rate, a humidifier heat source power, and/or a tube temperature.

At step 1624, the controller can combine the various sensors inputs and/or system parameters using certain algorithms to calculate a reverse flow prediction number. The process can advantageously improve confidence of reverse flow condition detection by combining these parameters, which individually may be predictive of a reverse flow condition at a lower confidence.

The process can evaluate, for example, the humidifier inlet temperature, an absolute value of a humidifier outlet temperature error (difference between the measured humidifier outlet temperature and set point), a ratio of the flow rate to the humidifier heat source power, a ratio of the measured humidifier inlet temperature to the humidifier outlet set point, and a ratio of the measured humidifier inlet temperature to the measured tube temperature. A person of ordinary skill in the art would appreciate from the disclosure herein that other ratios can be used. An example algorithm can obtain the reverse flow prediction number by calculating, for example, A*humidifier inlet temperature+B*|humidifier outlet temperature−humidifier outlet set point|+C*(flow rate÷humidifier heat source power)+D*(humidifier inlet temperature÷humidifier outlet set point)+E*(humidifier inlet temperature/tube temperature)+F, where A, B, C, D, E, and F can be coefficients. The coefficients can be derived empirically using a learning software, by experiments, and/or other methods. For example, the learning software can derive one or more of the coefficients from a number of reverse flow data sets and a number of forward flow data sets. The reverse and/or forward data sets can include different external conditions, such as the flow rate, ambient temperature, or others. The coefficients can vary depending on the parameters and/or the data sets provided to the learning software.

The process can also evaluate, for example, a filtered or unfiltered flow rate, the absolute value of a humidifier outlet temperature error (difference between the measured humidifier outlet temperature and set point), the ratio of the measured humidifier inlet temperature to the measured tube temperature, and a ratio of a filtered or unfiltered power to at least a portion of the inspiratory conduit heat source ("inspiratory conduit heat source power") to humidifier heat source temperature. A person of ordinary skill in the art would appreciate from the disclosure herein that other ratios can be used. An example algorithm can obtain the reverse flow prediction number by calculating, for example, G* filtered or unfiltered flow rate+H*|humidifier outlet temperature−humidifier outlet set point|+I*(humidifier inlet temperature/tube temperature)+J*(filtered or unfiltered inspiratory conduit heat source power/humidifier heat source temperature), where G, H, I, and J are coefficients that can be derived empirically. For example, G, H, I, and J can be derived in a similar manner as A, B, C, D, E, and F described above.

At step 1625, the controller can determine if the prediction number is greater than zero. If the prediction number is greater than zero, the controller can output an indication in step 1630 that there can be a reverse flow condition. If the prediction number is not greater than zero, no reverse flow is detected at step 1640. The system can output an indication that no reverse flow condition is detected, output no indication, and/or either begin a ventilation and/or humidification therapies or continue its current ventilation and/or humidification therapies at step 1640. Different thresholds other than the prediction number being greater than zero can be used for indicating a reverse flow condition. For example, a number of 0 or less can indicate forward flow. Any number between 0 and 100 can indicate a likelihood of a reverse flow condition, with a larger number indicating a greater likelihood of a reverse flow condition. In addition, a counter and/or accumulated value over time can be used to build up confidence. In an example, the system may require the prediction number to be above a threshold for a period of time to trigger the reverse flow alarm.

In another example, reverse flow can be detected by monitoring only a single parameter. For example, if a flow sensor reading is noticeably higher than expected, there is a likelihood of a reverse flow condition.

Although the passive and active processes are described herein with respect to reverse flow conditions in the humidifier and/or the inspiratory conduit, such as the humidifier 20 and/or in the inspiratory conduit 40 illustrated in FIGS. 2A-D, the processes can be used in various combinations to detect reverse flow conditions and errors in connections at various locations in the humidification system. Furthermore, one process can be used to verify if another process has correctly identified an indication of reverse flow conditions. The system can switch between passive and active detection processes, and/or switch among various processes when the system is in a passive detection mode or an active detection mode.

Other sensors can also be used, alternatively or additionally, for detecting reverse flow, such as using directional flow sensors as described above, differential pressure sensors, LASER Doppler, ultrasonic transducers, inlet and/or outlet humidity sensors, and/or mechanical sensors such as a flap, a lever, or a turbine:

When the humidification system detects multiple errors, the system can output the reverse flow alarm first. The multiple errors can include a reverse flow error and a water-out error. The reverse flow condition may need to be corrected before detection of other errors, such as the water-out error, can be more reliably detected. The system can improve a speed of alarm recovery by disabling the alarms when an abrupt change in the flow rate is detected.

Detection of Incorrect Expiratory Tube Connection

In respiratory therapies that require a dual-limb humidification system, it is important to monitor disconnection of the inspiratory conduit heat source in the expiratory conduit. As described above, the dual-limb humidification system can be used in substantially all of invasive therapies, about half of noninvasive adult therapies, about half of neonatal therapies, and potentially some pediatric therapies. Disconnection of the inspiratory conduit heat source in the expiratory conduit can occur during set-up and/or during use. The disconnection can be due to an improper and/or incomplete connection of the expiratory conduit to the patient interface, or misuse of the expiratory conduit by a user during set-up. The disconnection during use can be due to an accidental disconnection or misuse by a user.

For certain therapy modes, the inspiratory conduit heat sources on the inspiratory and expiratory conduits are each heated as a single wire ("single zone heating"). For example, the noninvasive adult therapy can be performed with a single zone heating of the inspiratory conduit. The humidification system can have two heat source drivers. Each driver can be configured to energize one of the two inspiratory conduit heat sources. The two inspiratory conduit heat sources can be energized at a low duty cycle and/or a minimum power, which one of skill in the art would understand to be any duty cycle that is high enough to supply sufficient power to produce a detectable current when the inspiratory conduit heat source is connected. A low power may be preferred since this is safer and minimises disruption to therapy. This disruption may be mitigated by applying the power for only a short amount of time. The low duty cycle may be in the range of about 1-50%, 1-25%, 1-10%, 2-15%, 3-10%, 4-9%, 2%, 3%, 4%, 5%, 6%, 7%, 8%, 9%, 10%, or any other suitable duty cycle. The driver for heating the expiratory conduit heat source can apply a voltage across the expiratory conduit heat source. The driver can monitor a current in the electrical circuit. If the current is at or near zero, the driver can output an expiratory conduit heat source disconnection alarm. The alarm can be in the manners described above. If the current is not at or near zero, the expiratory conduit heat source is connected to the circuit. The system can also detect disconnection of the expiratory conduit heat source by detecting a presence of a circuit ID resistor when the hardware and/or software controller applies a power across the expiratory conduit heat source. The system can determine that the expiratory conduit heat source is disconnected when the circuit ID resistor cannot be detected.

Figure 17A:
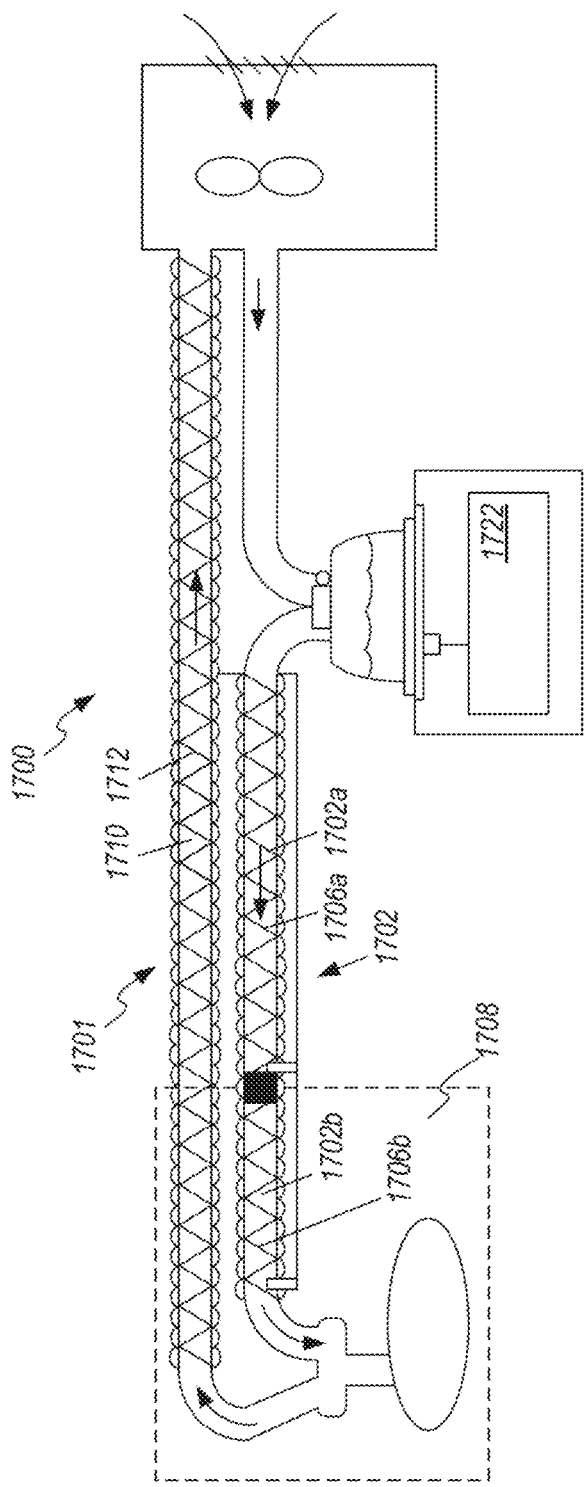
FIG. 17A illustrate an example dual-limb humidification system with a segmented inspiratory conduit.

For certain therapy modes, such as the neonatal therapy or other forms of therapy, the inspiratory conduit heat source can have more than a single zone heating. FIG. 17A illustrates an example neonatal therapy humidification system 1700. The respiratory humidification system 1700 can comprise a breathing circuit 1701 that includes a segmented inspiratory conduit 1702 and an expiratory conduit 1710. The expiratory conduit 1710 can comprise an expiratory heater wire 1712. The segmented inspiratory conduit 1702 can comprise first and second segments 1702a and 1702b. The first segment 1702a can include a first inspiratory heater wire 1706a. The second segment 1702b can include a second inspiratory heater wire 1706b.

The segments of the inspiratory limb 1702a, 1702b can be coupled to one another to form a single conduit for gas delivery. The first segment 1702a can be a portion of the inspiratory conduit 1602 that is outside an incubator 1708 and the second segment 1702b, or incubator extension, can be a portion of the inspiratory conduit 1702 that is inside the incubator 1708. The incubator 1708 can cause different temperatures along different segments of the inspiratory conduit 1702, such as in conjunction with a radiant warmer. The first and second inspiratory heater wires 1706a, 1706b can be used to provide different levels of heat to different segments 1702a, 1702b of the inspiratory conduit 1702 to reduce or prevent condensation and/or to control a temperature of gas delivered to a user.

Figure 17B:
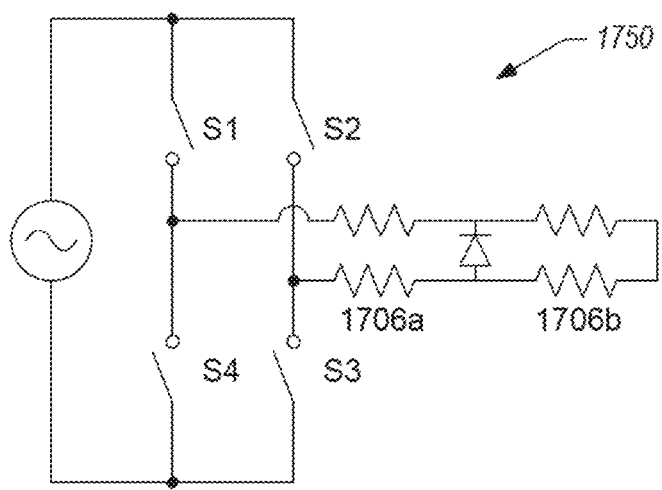
FIG. 17B illustrate an example circuit diagram configured to control two segments of an inspiratory conduit heat source in parallel using an active rectifier circuit.

A controller 1722 can be configured to switch between controlling the first inspiratory heater wire 1706a ("HW1"), or controlling both of the first and second inspiratory heater wires 1706a and 1706b ("HW2"). FIG. 17B illustrates an example circuit diagram 1750 for switching between heating HW1 and HW2 by altering the switching of the MOSFET pairs. The system 1700 can have two drivers for driving the expiratory heater wire 1712, HW1, and HW2. The first driver can energize HW1 and the expiratory heater wire 1712 in parallel. The second driver can energize HW2 and the expiratory heater wire 1712 in parallel. The disclosure of this method is useful in situations where the system includes more heater wires than heater wire drivers.

In order to detect a disconnection of the expiratory heater wire during use, at least one of the inspiratory heater wire drivers can monitor the current in the electrical circuits. The heaters wires can have known resistances or known resistance with tolerance. When one of the drivers is activated to apply a voltage across the inspiratory heater wires, the active driver can monitor the current in the electrical circuit. The driver can apply the voltage across the expiratory heater wire and HW1, or the expiratory heater wire and HW2. If the current is not at or near an expected value based on the known voltage, and/or if there is any sudden changes in the current, one or more of the inspiratory heater wires may have been disconnected. The current may not at or near an expected value based on the known voltage when the current deviates from the expected value by a predetermined tolerance. Sudden changes can occur when the change(s) in the current exceed(s) a threshold. The current through the inspiratory heater wires can be lower when the expiratory heater wire is properly connected to the circuit than when the expiratory heater wire is disconnected. This can be because the properly connected expiratory heater wire reduces the overall resistance of the circuit.

When the controller observes the current deviating from the expected value and/or sudden current (and therefore resistance) changes, the controller can exit the therapy mode. The controller can output an indication of exiting the therapy mode. The controller can proceed to use the one inspiratory heater wire per driver detection process described above as if the inspiratory heater wire provides a single zone heating. Specifically, the controller can switch to a configuration that reconnects the heater wire drivers to one heater wire per driver and observe the current across the expiratory heater wire.

The humidification system can have adjustable expiratory conduit heat source, such as expiratory heater wire of FIG. 17A, disconnection alarm settings based on the therapy mode. The expiratory conduit heat source disconnection alarm can remain activated in therapies that substantially always use a dual-limb system. The alarm can remain active by default in some dual-limb systems, for example, for invasive therapies. The expiratory conduit heat source disconnection alarm can be activated at predetermined intervals, and/or remain disabled in therapies that do not substantially always use a dual-limb system. The intervals can be preprogrammed intervals and/or user-determined intervals. The alarm can remain disabled by default in some systems, for example, for noninvasive adult therapies or neonatal therapies.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. Additionally, as used herein, "gradually" has its ordinary meaning, for example, differing from a non-continuous change, such as a step-like change.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A method of detecting reverse flow in a respiratory humidification system, the method comprising:
    using one or more hardware processors of the humidification system to control circuitry configured to power a heating element of the humidification system, providing electrical power to the heating element, the humidification system further comprising a gases source, a humidifier including an inlet and an outlet, and an inspiratory conduit including an inspiratory conduit heat source, the humidifier further including a humidifier heat source;
    comparing a first temperature gradient measured by a first sensor downstream of the heating element with a second temperature gradient measured by a second sensor upstream of the heating element, the first and second sensors in electrical communication with the one or more hardware processors; and
    outputting to a display of the humidification system an indication of reverse flow conditions when the second temperature gradient is higher than the first temperature gradient.

2. The method of claim 1, further comprising:
    providing another electrical power to a humidifier heat source of the humidifier of the humidification system;
    receiving sensor data from a humidifier heat source temperature sensor at or near the humidifier heat source, the humidifier heat source temperature sensor in electrical communication with the one or more hardware processors;
    comparing a temperature gradient at the humidifier heat source with a threshold temperature gradient; and
    outputting to the display of the humidification system an indication of humidifier water-out condition when the temperature gradient at the humidifier heat source is higher than the threshold temperature gradient.

3. The method of claim 1, wherein the method further comprises prior to comparing the first temperature gradient with the second temperature gradient, controlling a duty cycle to the inspiratory conduit heat source.

4. The method of claim 3, wherein the method further comprises controlling the duty cycle to the inspiratory conduit heat source to 100%.

5. The method of claim 1, wherein the method further comprises prior to comparing the first temperature gradient with the second temperature gradient, controlling a duty cycle to the humidifier heat source.

6. The method of claim 5, wherein the method further comprises controlling the duty cycle to the humidifier heat source to 0%.

7. The method of claim 1, wherein the method further comprises interrupting a therapy that is run on the humidification system when indicating reverse flow conditions in the humidification system, the therapy being a respiratory or ventilation therapy or a humidification therapy.

8. The method of claim 7, wherein the method further comprises resuming the therapy after outputting the indication of reverse flow conditions and rectifying the reverse flow conditions.

9. The method of claim 1, wherein the method further comprises alerting a user of the indication of reverse flow conditions, the alerting comprising one or both of: providing one or more audible alarms, text message, images, or a combination thereof; or providing instructions for resolving the reverse flow condition.

10. The method of claim 1, wherein the humidification system comprises an expiratory conduit.

11. The method of claim 1, wherein the method further comprises checking for a sudden change in a flow rate when outputting the indication of reverse flow conditions and/or when a reverse flow error alarm is activated.

12. The method of claim 11, wherein the method further comprises disabling the indication of reverse flow conditions if the sudden change in the flow rate is detected.

13. The method of claim 12, wherein checking for the sudden change in the flow rate comprises detecting whether there is no flow in the respiratory humidification system.

14. The method of claim 1, wherein the heating element comprises one or both of an inspiratory conduit heat source or a humidifier heat source.

15. A respiratory humidification system with reverse flow detection, the respiratory humidification system comprising:
 a gases source configured to provide a source of gases;
 a humidifier including an inlet and an outlet, the humidifier configured to humidify air and further including a humidifier heat source to heat a liquid to humidify the gases provided by the gases source;
 an inspiratory conduit configured to provide the humidified gases to a user and including an inspiratory conduit heat source, the gases source, humidifier and inspiratory conduit forming at least a part of a breathing circuit;
 a first sensor downstream of the humidifier heat source and/or the inspiratory conduit heat source and configured to measure a first temperature;
 a second sensor upstream of the humidifier heat source and/or the inspiratory conduit heat source and configured to measure a second temperature; and
 a hardware and/or software controller, the hardware and/or software controller in electrical communication with the first and second sensors, the hardware and/or software controller configured to detect an indication of reverse flow conditions in the humidification system by:
  providing an electrical power to the humidifier heat source and/or the inspiratory conduit heat source;
  comparing a first temperature gradient at the first sensor with a second temperature gradient at the second sensor; and
  outputting an indication of reverse flow conditions when the second temperature gradient is higher than the first temperature gradient.

16. The respiratory humidification system of claim 15, wherein the hardware and/or software controller is further configured to detect a humidifier water-out condition by:
 providing another electrical power to the humidifier heat source;
 receiving sensor data from a humidifier heat source temperature sensor at or near the humidifier heat source, the humidifier heat source temperature sensor in electrical communication with the hardware and/or software controller;
 comparing a temperature gradient at the humidifier heat source with a threshold temperature gradient; and
 outputting an indication of humidifier water-out condition when the temperature gradient at the humidifier heat source is higher than the threshold temperature gradient.

17. The respiratory humidification system of claim 15, wherein the first sensor is located at the outlet of the humidifier or the inlet of the humidifier and the second sensor is located at a patient end of the inspiratory conduit or the outlet of the humidifier.

18. The respiratory humidification system of claim 15, wherein the hardware and/or software controller is configured to interrupt a therapy that is run on the humidification system when indicating reverse flow conditions in the humidification system, the therapy being a respiratory or ventilation therapy or a humidification therapy.

19. The respiratory humidification system of claim 15, wherein the hardware and/or software controller is configured to detect an indication of reverse flow conditions in the humidification system further by:
 prior to comparing the first temperature gradient with the second temperature gradient, controlling a duty cycle to the inspiratory conduit heat source to 100%.

20. The respiratory humidification system of claim 15, wherein the hardware and/or software controller is configured to detect an indication of reverse flow conditions in the humidification system further by:
 prior to comparing the first temperature gradient with the second temperature gradient, controlling a duty cycle to the humidifier heat source to 0%.

* * * * *